(12) United States Patent
Murdoch et al.

(10) Patent No.: US 10,234,410 B2
(45) Date of Patent: *Mar. 19, 2019

(54) STABLE BINARY NANOCRYSTALLINE ALLOYS AND METHODS OF IDENTIFYING SAME

(75) Inventors: Heather A. Murdoch, Baltimore, MD (US); Christopher A. Schuh, Wayland, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 812 days.

This patent is subject to a terminal disclaimer.

(21) Appl. No.: 14/384,518

(22) PCT Filed: Mar. 12, 2012

(86) PCT No.: PCT/US2012/028811
§ 371 (c)(1),
(2), (4) Date: Sep. 11, 2014

(87) PCT Pub. No.: WO2013/137857
PCT Pub. Date: Sep. 19, 2013

(65) Prior Publication Data
US 2015/0125338 A1    May 7, 2015

(51) Int. Cl.
*G01N 1/00*     (2006.01)
*G01N 25/12*    (2006.01)
(Continued)

(52) U.S. Cl.
CPC ........... *G01N 25/12* (2013.01); *C22C 1/00* (2013.01); *C22C 5/02* (2013.01); *C22C 5/04* (2013.01);
(Continued)

(58) Field of Classification Search
None
See application file for complete search history.

(56) References Cited

U.S. PATENT DOCUMENTS 7,292,958 B2    11/2007 Ceder et al.
7,520,944 B2     4/2009 Johnson
(Continued)

FOREIGN PATENT DOCUMENTS

| CN | 1958839 A | 5/2007 |
|---|---|---|
| WO | WO 2005/005675 A2 | 1/2005 |
| WO | WO 2013/137857 A2 | 9/2013 |

OTHER PUBLICATIONS

Kris A. Darling et al., Conference Presentation entitled "Grain Size Stabilization in Nanostructured Copper Alloys" given at The Minerals, Metals & Materials Society (TMS) 2011 Annual Conference, San Diego, CA, Mar. 1, 2011.*

(Continued)

*Primary Examiner* — Deborah Yee
(74) *Attorney, Agent, or Firm* — Wolf, Greenfield & Sacks, P.C.

(57) ABSTRACT

Identifying a stable phase of a binary alloy comprising a solute element and a solvent element. In one example, at least two thermodynamic parameters associated with grain growth and phase separation of the binary alloy are determined, and the stable phase of the binary alloy is identified based on the first thermodynamic parameter and the second thermodynamic parameter, wherein the stable phase is one of a stable nanocrystalline phase, a metastable nanocrystalline phase, and a non-nanocrystalline phase.

7 Claims, 15 Drawing Sheets

(51) Int. Cl.

| | | |
|---|---|---|
| G01N 25/02 | (2006.01) | |
| G01N 33/20 | (2006.01) | |
| C22C 1/02 | (2006.01) | |
| C22C 33/00 | (2006.01) | |
| C22C 33/04 | (2006.01) | |
| C22C 1/00 | (2006.01) | |
| C22C 5/02 | (2006.01) | |
| C22C 5/04 | (2006.01) | |
| C22C 5/06 | (2006.01) | |
| C22C 7/00 | (2006.01) | |
| C22C 11/00 | (2006.01) | |
| C22C 12/00 | (2006.01) | |
| C22C 13/00 | (2006.01) | |
| C22C 16/00 | (2006.01) | |
| C22C 20/00 | (2006.01) | |
| C22C 22/00 | (2006.01) | |
| C22C 24/00 | (2006.01) | |
| C22C 27/00 | (2006.01) | |
| C22C 27/02 | (2006.01) | |
| C22C 27/04 | (2006.01) | |
| C22C 27/06 | (2006.01) | |
| C22C 28/00 | (2006.01) | |
| C22C 38/00 | (2006.01) | |
| C22C 43/00 | (2006.01) | |

(52) U.S. Cl.
CPC ............... *C22C 5/06* (2013.01); *C22C 7/00* (2013.01); *C22C 11/00* (2013.01); *C22C 12/00* (2013.01); *C22C 13/00* (2013.01); *C22C 16/00* (2013.01); *C22C 20/00* (2013.01); *C22C 22/00* (2013.01); *C22C 24/00* (2013.01); *C22C 27/00* (2013.01); *C22C 27/02* (2013.01); *C22C 27/025* (2013.01); *C22C 27/04* (2013.01); *C22C 27/06* (2013.01); *C22C 28/00* (2013.01); *C22C 38/002* (2013.01); *C22C 43/00* (2013.01); *G01N 25/02* (2013.01); *G01N 33/20* (2013.01)

(56) References Cited

U.S. PATENT DOCUMENTS

| | | |
|---|---|---|
| 9,791,394 B2 | 10/2017 | Murdoch et al. |
| 2003/0041801 A1 | 3/2003 | Hehmann |
| 2003/0183306 A1 | 10/2003 | Hehmann et al. |
| 2006/0074594 A1 | 4/2006 | Ceder et al. |
| 2006/0191611 A1 | 8/2006 | Johnson |
| 2007/0276638 A1 | 11/2007 | Borchers et al. |
| 2010/0278682 A1 | 11/2010 | Sasaki et al. |
| 2011/0277890 A1 | 11/2011 | Bledsoe et al. |
| 2012/0232858 A1 | 9/2012 | Zhou et al. |
| 2012/0270737 A1 | 10/2012 | Sutter et al. |
| 2013/0133793 A1 | 5/2013 | McDevitt |
| 2014/0026776 A1 | 1/2014 | Kecskes et al. |
| 2014/0276638 A1 | 9/2014 | Steen et al. |
| 2014/0283963 A1 | 9/2014 | Gao et al. |
| 2014/0348203 A1 | 11/2014 | Murdoch et al. |
| 2015/0375301 A1 | 12/2015 | Darling et al. |
| 2018/0100817 A1 | 4/2018 | Murdoch et al. |

OTHER PUBLICATIONS

Jason R. Trelewicz et al., "Grain boundary segregation and thermodynamically stable binary nanocrystalline alloys," Physical Review B 79, 094112 (2009), pp. 1-13.*

"A predictive model for thermodynamic stability of grain size in nanocrystalline ternary alloys," Mostafa Saber et al., J. Appl. Physics, 114, 103510 (2013).*

U.S. Appl. No. 61/604,924, filed Feb. 29, 2012 by Darling et al.*

"Thermodynamics and Phase Diagrams," Chapter 3, Phase Diagrams—Understanding the Basics, F.C. Campbell,editor, copyright 2012 ASM International, www.asminternational.org, Mar. 2, 2012.*

"Alloys created between immiscible elements" Progress in Material Science 50 (2005) pp. 413-509.*

"Stabilized nanocrystalline iron-based alloys: Guiding efforts in alloy selection", Materials Science and Engineering A, K.A. Darling et al., Oct. 1, 2010.*

Chinese Office Action dated Jul. 22, 2016 for Application No. 201480029395.6.

Binder et al., "Computer Experiments on Phase Separation in Binary Alloys", Advances in Colloid and Interface Science, vol. 10, pp. 173-214, 1979.

Chen, "Phase-Field Models for Microstructure Evolution," Annual Review of Materials Research, vol. 32, pp. 113-140, Aug. 2002.

Eckert et al., "Thermal Stability and Grain Growth Behavior of Mechanically Alloyed Nanocrystalline Fe—Cu Alloys," Journal of Applied Physics, vol. 73, pp. 131-141, Jan. 1993.

International Search Report and Written Opinion dated Jul. 6, 2012 issued in connection with International Application No. PCT/US2012/028811.

Invitation to Pay Additional Fees dated Sep. 4, 2014 in Application No. PCT/US2014/038781.

International Search Report and Written Opinion dated Nov. 18, 2014 for Application No. PCT/US2014/038781.

International Preliminary Report on Patentability dated Sep. 25, 2014 in Application No. PCT/US2012/028811.

Extended European Search Report dated Dec. 21, 2016 for Application No. EP14801372.5.

Office Communication for U.S. Appl. No. 14/282,691 dated Dec. 27, 2016.

Bryden et al., Thermal stability and hydrogen absorption characteristics of palladium-yttrium nanoalloys. Acta Materialia. 1996; 44(9): 3847-3854.

Koch et al., Stabilization of nanocrystalline grain sizes by solute additions. J Mater Sci. Dec. 2008, 43(23): 7264-7272.

Murdoch et al., Stability of binary nanocrystalline alloys against grain growth and phase separation. Acta Materialia. Apr. 2013; 61(6): 2121-2132.

Chinese Office Action dated Mar. 3, 2017 for Application No. 201480029395.6.

Notice of Allowance for U.S. Appl. No. 14/282,691 dated Apr. 26, 2017.

Chinese Office Action dated Feb. 24, 2018 for Application No. 201611044120.7.

Office Communication dated Apr. 13, 2018 for U.S. Appl. No. 15/659,515.

Chinese Office Action dated Dec. 4, 2018 for Chinese Patent Application No. 201611044120.7.

Fan et al., Metallurgical and Materials Thermodynamics, Beijing: Metallurgical Industry Press, Jul. 2012, pp. 334-336.

* cited by examiner (a)

(b)

STABLE BINARY NANOCRYSTALLINE ALLOYS AND METHODS OF IDENTIFYING SAME

STATEMENT REGARDING FEDERALLY SPONSORED RESEARCH

This invention was made with Government support under Grant Nos. W911NF-07-D-0004, W911QX-09-P-0009 and W911NF-09-1-0422 awarded by the United States Army. The Government has certain rights in this invention.

CROSS REFERENCE TO RELATED APPLICATIONS

The present application is the U.S. National Stage of International Application No. PCT/US2012/028811, filed on Mar. 12, 2012, the content of which is incorporated by reference herein in its entirety.

All publications, patents, and patent applications cited in this Specification are hereby incorporated by reference in their entirety.

BACKGROUND

Pure nanocrystalline metals generally lack structural stability due to the energy associated with their high volume fraction of grain boundaries, often exhibiting grain growth even at room temperature. However, the addition of solute atoms can stabilize the nanostructure against grain growth. The mechanism for this improvement in stability has been proposed to involve the reduction of grain boundary energy through the segregation of solute atoms to the grain boundaries, with possible secondary kinetic contributions based on solute drag. Accordingly, alloying has emerged as a critical component for the development and deployment of nanocrystalline materials, although our basic understanding of stability in nanocrystalline alloys remains incomplete.

A number of models pertaining to grain boundary segregation in nanocrystalline systems have been developed. Starting from the Gibbs adsorption equation, Weissmuller noted that the segregation of solute atoms to the grain boundaries in a dilute system reduces the grain boundary energy, $\gamma$:

$$\gamma = \gamma_0 - \Gamma(\Delta H_{seg} + kT \log [X]) \quad (1)$$

where the reduction in grain boundary energy from the unalloyed condition, $\gamma_0$, is a function of the heat of segregation for the binary system ($\Delta H_{seg}$) and the solute excess ($\Gamma$) at the grain boundary for a particular global solute concentration (X) and temperature (T), with k the Boltzmann constant.

While the grain size-solute content relationships it predicted were promising with respect to experimental evidence, the stability of nanocrystalline systems was evaluated only with respect to changes in grain size. In fact, all of the analytical models to date suffer this deficiency. Suppression of grain growth is an important criterion for stabilizing a nanostructured alloy, but a potentially equally important stability is that with respect to phase separation. Even if a nanocrystalline alloy with grain boundary segregation is relatively more stable than a coarse-grained alloy of the same composition, the nanocrystalline state may never be achievable if the system phase separates.

SUMMARY

In view of the foregoing, the Inventors have recognized and appreciated the advantages of the capability of predicting stable binary nanocrystalline alloys including having a binary alloy in a stable nanocrystalline phase against both grain growth and phase separation.

Accordingly, provided in one embodiment is a method of identifying a stable phase of a binary alloy comprising a solute element and a solvent element, the method comprising: (A) determining at least two thermodynamic parameters associated with grain growth and phase separation of the binary alloy; and (B) identifying the stable phase of the binary alloy based on the first thermodynamic parameter and the second thermodynamic parameter, wherein the stable phase is one of a stable nanocrystalline phase, a metastable nanocrystalline phase, and a non-nanocrystalline phase.

Provided in another embodiment is an article, comprising: a diagram delineating a plurality of regions respectively representing different stable phases of at least one binary alloy, wherein: the different stable phases of the at least one binary alloy include at least one of a stable nanocrystalline phase, a metastatic nanocrystalline phase, and a non-nanocrystalline phase; and the respective regions of the plurality of regions are delineated by at least one boundary determined as a function of at least two thermodynamic parameters associated with grain growth and phase separation of the at least one binary alloy.

Provided in another embodiment is a method of identifying a stable phase of a binary alloy comprising a solute element and a solvent element, the method comprising: (A) determining at least two thermodynamic parameters associated with grain growth and phase separation of the binary alloy; (B) comparing the at least two thermodynamic parameters with a diagram delineating a plurality of regions respectively representing predetermined different stable phases of at least one predetermined binary alloy, wherein: the predetermined different stable phases of the at least one predetermined binary alloy include at least one of a stable nanocrystalline phase, a metastable nanocrystalline phase, and a non-nanocrystalline phase; and the respective regions of the plurality of regions are delineated by at least one boundary determined as a function of at least two thermodynamic parameters associated with grain growth and phase separation of the at least one predetermined binary alloy; and (C) identifying the stable phase of the binary alloy based on the comparison.

Provided in another embodiment is a composition, comprising a nanocrystalline binary alloy; wherein the alloy is stable against grain growth and phase separation at a predetermined temperature.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
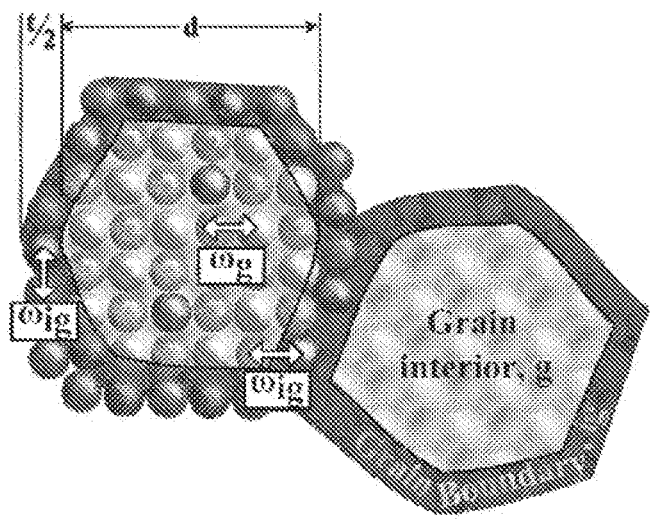
FIG. 1 provides a schematic of two nanocrystalline grains exhibiting grain boundary segregation; grey atoms represent solvent atoms and red atoms represent solute atoms.

Following below are more detailed descriptions of various concepts related to, and embodiments of, inventive stable binary nanocrystalline alloys and methods of predicting same. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Provided in one embodiment are methods and articles, including a nanocrystalline solution model, that may be employed to identify the conditions under which binary nanocrystalline alloy systems with positive heats of mixing are stable with respect to both grain growth (segregation reduces the grain boundary energy to zero) and phase separation (the free energy of the nanocrystalline system is lower than the common tangent defining the miscibility gap). In another embodiment, a "nanocrystalline stability map" is calculated in terms of alloy thermodynamic parameters. At least three main regions may be delineated in these maps: one where grain boundary segregation does not result in a stabilized nanocrystalline structure, one in which phase separation would be preferential (despite the presence of a nanocrystalline state stable against grain growth), and one for which the nanocrystalline state is stable against both grain growth and phase separation. Additional details about the stabilized structures are also presented in the map, which can be regarded as tools for the design of stable nanocrystalline alloys.

One embodiment described herein is related to a method of identifying a stable phase of a binary alloy; the stable phase may be one of a stable nanocrystalline phase, a metastable nanocrystalline phase, and a non-nanocrystalline phase. Each of these phases are described in detail below.

The term "nanocrystalline" herein refers to the size of a crystal (or a "grain") being less than or equal to about 1000 nm—e.g., 500 nm, 200 nm, 100 nm, 50 nm, 20 nm, 10 nm, 5 nm, 2 nm, etc. For example, the grain size may be between 1000 nm and about 2 nm—e.g., about 500 nm and about 2 nm, about 200 nm and about 2 nm, about 100 nm and about 2 nm, about 50 nm and about 2 nm, about 30 nm and about 2 nm, about 20 and about 2 nm, about 10 nm and about 2 nm. In some embodiments, the size may refer to the largest dimension of the grain. The size of the grains referred herein may be determined as an "average" and may be measured by any suitable techniques. The dimensions may refer the diameter, length, width, height, depending on the geometry of the grain. In some instances (and as provided below), a stable nanocrystalline material may also refer to a material comprising an amorphous phase.

The alloy described herein may be a binary alloy, ternary alloy, or an alloy with a higher number of constituents. In some embodiments, a binary alloy may contain a solute element (or solute atoms) and a solvent element (or solvent atoms). While the main constituents of a binary alloy are the solute and the solvent elements, some incidental minute trace amount of impurity element(s) may also be present. The designation of a solute versus a solvent element need not be rigid. In general, the constituent element in the alloy that has the higher amount may be considered as the solvent element, while the other that has the lower amount may be considered as the solute element. The amount may refer to either atomic percentage or weight percentage.

The determination of the stable phase may involve the determination of a plurality of thermodynamic parameters. In some embodiments, the determination involves the determination of at least two thermodynamic parameters—e.g., three, four, or more. Each of the thermodynamic parameters may be associated with one or more phenomenons (e.g., physical phenomenon) related to the alloy. For example, the at least two thermodynamic parameters may be associated with grain growth and phase separation of the binary alloy. As described further below, based upon the thermodynamic parameters, the presently described article, systems, and methods may provide a mechanism to identify the stable phase of the alloy.

The term "stable phase" herein of an alloy refers to a phase of the alloy that is present because it is favored energetically based on thermodynamics. In some embodiments, the stable phase occurs when the thermodynamic parameter(s) (e.g., free energy of mixing, enthalpy of mixing, enthalpy of segregation, etc.) associated therewith is at a minimum. Other thermodynamic parameters may be employed, and depending on the parameters selected, they may be affected by other variables. For example, a thermodynamic parameter may be a free energy of mixing, which may be a function of at least one of (i) concentration of grain boundary in the binary alloy, (ii) grain size of the binary alloy, (iii) concentration of the solute element in the binary alloy, and (iv) concentration of the solvent element in the binary alloy.

Accordingly, when the alloy is stable (thermodynamically) as a stable nanocrystalline phase, the alloy will take the form of a nanocrystalline alloy. Alternatively, when the alloy is stable as a metastable nanocrystalline phase, as will be described below, two competing driving forces take place: while one thermodynamic parameter of the alloy favors a nanocrystalline phase, another parameter favors phase separation (and thus no nanocrystalline phase). Thus, the alloy is only metastable and any stimulus that may cause an energy fluctuation may drive the alloy system towards a non-nanocrystalline phase. In yet another embodiment, when the alloy is stable as a non-nanocrystalline phase, the alloy will take the form of a non-nanocrystalline alloy, as the non-nanocrystalline phase is the phase energetically favored by thermodynamics.

Modified Regular Nanocrystalline Solution (RNS) Model

A model by Trelewicz proposes a regular nanocrystalline solution (RNS) model for the free energy of mixing in binary alloys with both crystalline and intercrystalline atomic environments. The RNS model reduces to a regular solution model for the crystalline phase in the limit of infinite grain size and to a standard grain boundary segregation isotherm in the dilute limit. However, the model by Trelewicz, along with all of the other models to date, evaluates only changes in grain size. This type of evaluation suffers the deficiency of not being able to account for phase separation.

While suppression of grain growth is an important criterion for stabilizing a nanostructured alloy, an equally important factor for stability is suppression of phase separation. For example, even if a nanocrystalline alloy with grain boundary segregation is relatively more stable than a coarse-grained alloy of the same composition, the nanocrystalline state may not be achievable if the system phase separates. Additionally, in some instances, second phase formation may become precursor to runaway grain growth, thereby becoming a cause of instability in alloyed nanocrystalline systems.

Accordingly, building upon the Trelewicz RNS model but in contrast thereto, the methods and articles described herein evaluate and predict alloy systems based upon the thermodynamic parameters associated with not only grain growth but also phase separation. The model utilized by the presently described methods, systems, and articles according to one embodiment is described as follows:

An intergrainular region (ig) and a region in the grain interior (g) with the total solute concentration, X, are defined, satisfying the balance:

$$X = f_{ig} X_{ig} + (1 - f_{ig}) X_g; \quad (2)$$

where $X_{ig}$ is the concentration of solute species in the intergrainular region, $X_g$ is the concentration in the grains, and $f_{ig}$ is the volume fraction of the intergrainular region:

$$f_{ig} = 1 - \left(\frac{d-t}{d}\right)^D, \quad (3)$$

where d is the grain diameter, t is the thickness of the grain boundary region (taken to be 0.5 nm in some embodiments but may be any other suitable values), and D is the dimensionality of the grain structure (taken, to be D=3 in some embodiments but may be any other suitable values). The model herein also describes a transition region referring to the bonds between the atoms in the grain and in the intergrainular region.

The analytical developments of the RNS model are statistical and envision the system as a population of atoms and bonds as illustrated on the left of FIG. 1; FIG. 1 shows the interaction between a pair of atoms and the parameter describing their interaction in one embodiment. Note that while the schematic on the left of FIG. 1 provides a view of discrete atoms, the system in general may be viewed as a continuum as shown on the right of FIG. 1. The spatial distribution of atomic bonds between the three regions, the energies associated with creating grain boundaries, and region-weighted entropic contributions may be encapsulated in the final free energy function derived from the model:

$$\Delta G_{mix} = (1 - f_{ig}) \Delta G^g_{mix} + f_{ig} \Delta G^{ig}_{mix} + \quad (4)$$

$$z \nu f_{ig} \Big[ [X_{ig}(X_{ig} - X_g) - (1 - X_g)(X_{ig} - X_g)] \omega_{ig} - $$

-continued $$\frac{1}{zt(X_{ig} - X_g)(\Omega_{\gamma B} - \Omega_{\gamma A})}\Big],$$

where z is the coordination number of the bulk material, $\Omega$ is the atomic volume, $\nu$ is the transitional bond fraction (the fraction of atoms contributing hands to the transitional bonding region), and $\omega$ is the Interaction parameter defined as:

$$\omega = E^{AB} - \frac{E^{AA} + E^{BB}}{2} \omega = E_{AB} - \frac{E_{AA} + E_{BB}}{2} \quad (5)$$

Two separate interaction parameters may be used to describe the binary nanocrystalline system: a bulk parameter $\omega_g$ describing the grain interior and $\omega_{ig}$ describing the interactions in the grain boundary and transition regions. This intergrainular interaction may or may not differ in character from that in the bulk. A positive interaction parameter denotes a phase separating system—i.e., where the energy of AB bonds is greater than the average of AA and BB bonds (A and B represent different types of atoms). The interaction parameter may be related to the heat of mixing via:

$$\Delta H_{mix} = z\omega_g X(1-X). \quad (6)$$

In some embodiments, a miscibility gap with a larger interaction parameter may exhibit a higher critical temperature ($T_{cr}$) and a lower solubility limit. $T_{cr}$ is the critical temperature defined at the top of a miscibility gap according to one embodiment.

The terms $\Delta G_{mix}^g$ and $\Delta G_{mix}^{ig}$ represent the outer boundaries of the system according to one embodiment. As an illustration, if the material contains only grain interior (d→∞, $f_{ig}$→0), the free energy function reduces to that of a classical regular solution:

$$\Delta G_{mix}^g = z\omega_g X_g(1-X_g) + kT[X_g \ln X_g + [(1-X]_g)\ln(1-X_g)]. \quad (7)$$

On the other hand, at the lower limit (or boundary) of grain size (d=t) is the free energy term of the intergrainular regular solution, which may include a dependence on the grain boundary energies of both grain and grain boundaries:

$$\Delta G_{mix}^{ig} = z\omega_{ig} X_{ig}(1 - X_{ig}) + \frac{\Omega}{t}(1 - X_{ig})\gamma_A +$$
$$\frac{\Omega}{t}X_{ig}\gamma_B kT[X_{ig}\ln X_{ig} + [((1 - X)]_{ig})\ln(1 - X_{ig})]. \quad (8)$$

Figure 2:
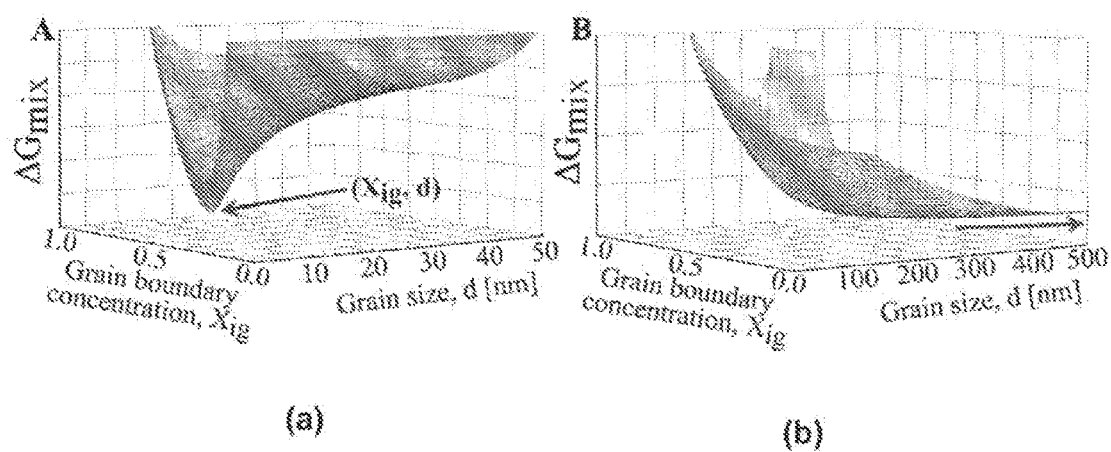
FIGS. 2(a)-2(b) show Gibbs free energy mixing surface for respectively a single value of global solute concentration and for no presence of nanocrystalline minimum.

The remaining terms in Eq. (4) describe the transition region. In some embodiments, the model described herein may be used to identify nanocrystalline alloys with segregation states that lead to formal stability against coarsening. Building upon the Trelewicz model, the model described herein also may generate a free-energy surface as shown in FIGS. 2(a)-2(b), plotted as a function of grain size (d) and intergrainular concentration ($X_{ig}$) at a constant global solute content and temperature. The minimum of the curve (shown larger in FIG. 3) represents a grain size and intergranular solute concentration at which the grain boundary energy for the given global solute concentration is zero. FIG. 2(b) shows a free energy surface with no nanocrystalline minimum present; the minimum value corresponds to that of the bulk regular solution (infinite grain size).

For certain combinations of input parameters (e.g., interaction parameters $\omega$, global concentration and temperature), the free-energy surface may exhibit a global minimum at a pair value of ($X_{ig}$, d), for which the nanocrystalline microstructure is stable. See FIG. 2(a). The minimum on the concentration axis ($X_{ig}$) shows the segregation state that is neither over- nor under-full (i.e., ideally saturated with solute). The minimum with respect to grain size corresponds to an alloy grain boundary energy of zero, and demonstrates a nanostructure that is stable with respect to grain growth. The existence of a minimum in the free energy surface depends on the materials' parameters and the solute content of the system. There may be cases where a nontrivial minimum does not exist (e.g., FIG. 2(b)), for which the "preferred" grain size is infinite, and the free energy of the system matches that of a bulk regular solution for the same global solute content.

As described above, the RNS model by Trelewicz is modified herein to account for not only grain growth, but also phase separation. In some embodiments, a comparison is performed for a given minimum-energy configuration of the kind as shown in FIG. 2(a), which only considers segregated nanocrystalline solid solution configurations for a single composition, against other possible configurations that involve phase separation.

In some embodiments, the free energy surface constructed for a discrete value of global solute content (i.e., of the kind shown in FIG. 2(a)), with a minimum at a given value of grain boundary composition and grain size, ($X_{ig}$, d) is evaluated. The examination of the region of the minimum in such a surface in one embodiment is illustrated in FIG. 3, in which the values of $X_{ig}$ and d are held constant and the global composition, X, is varied.

Figure 3:
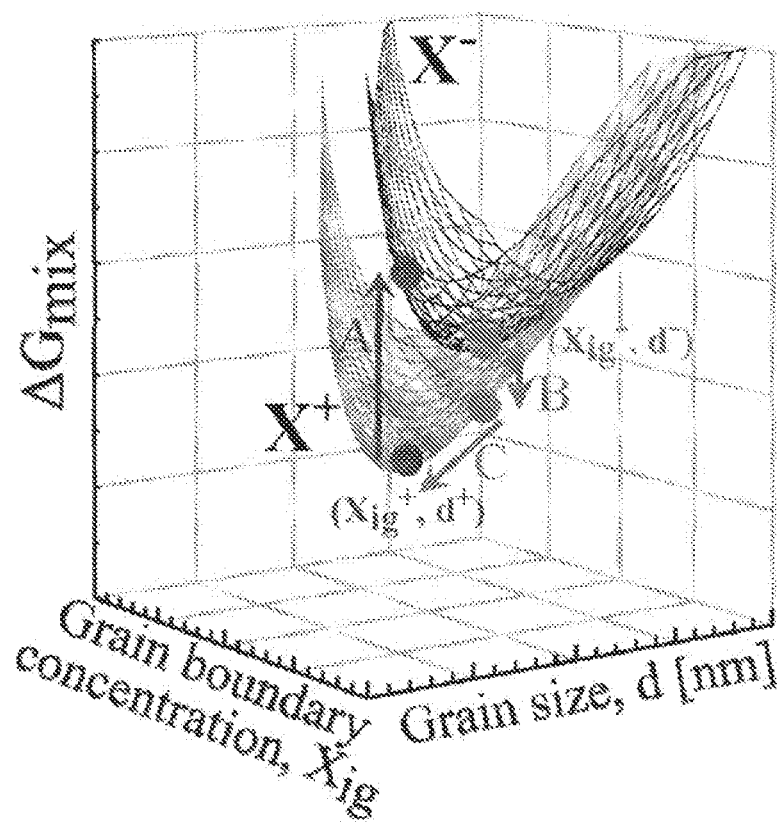
FIG. 3 shows minima in the free energy surface for two global solute concentrations, $X^+$ and $X^-$. See FIG. 4 for an alternative presentation.

For the purposes of illustration in FIG. 3, consider two global compositions, $X^+$ and X, slightly different from one another, to which two global compositions may be compared. At the global concentration $X^+$, a minimum occurs in the free energy surface (lower magenta curve in FIG. 3) at a specific value of intergranular concentration and grain size, ($X_{ig}^+$, d$^+$). If the global composition is decreased to X for the values ($X_{ig}^+$, d$^+$), the free energy increases. In one embodiment, this increase may be rapid with respect to even small changes in global composition, as shown by the arrow A in FIG. 3; this is similar to the free energy behavior of a stoichiometric line compound phase, with a single preferred composition for which the energy is minimized. On the other hand, if we instead start with the global composition $X^-$, with the minimum at ($X_{ig}^-$, d$^-$) and increase the composition (FIG. 3, arrow B), the grain boundary energy drops to less than zero, indicating that the grain size would prefer to decrease. On this new free energy surface for the higher composition ($X^+$), the system can decrease its energy by obtaining a new minimum (FIG. 3, arrow C) at a smaller grain size.

Figure 4:
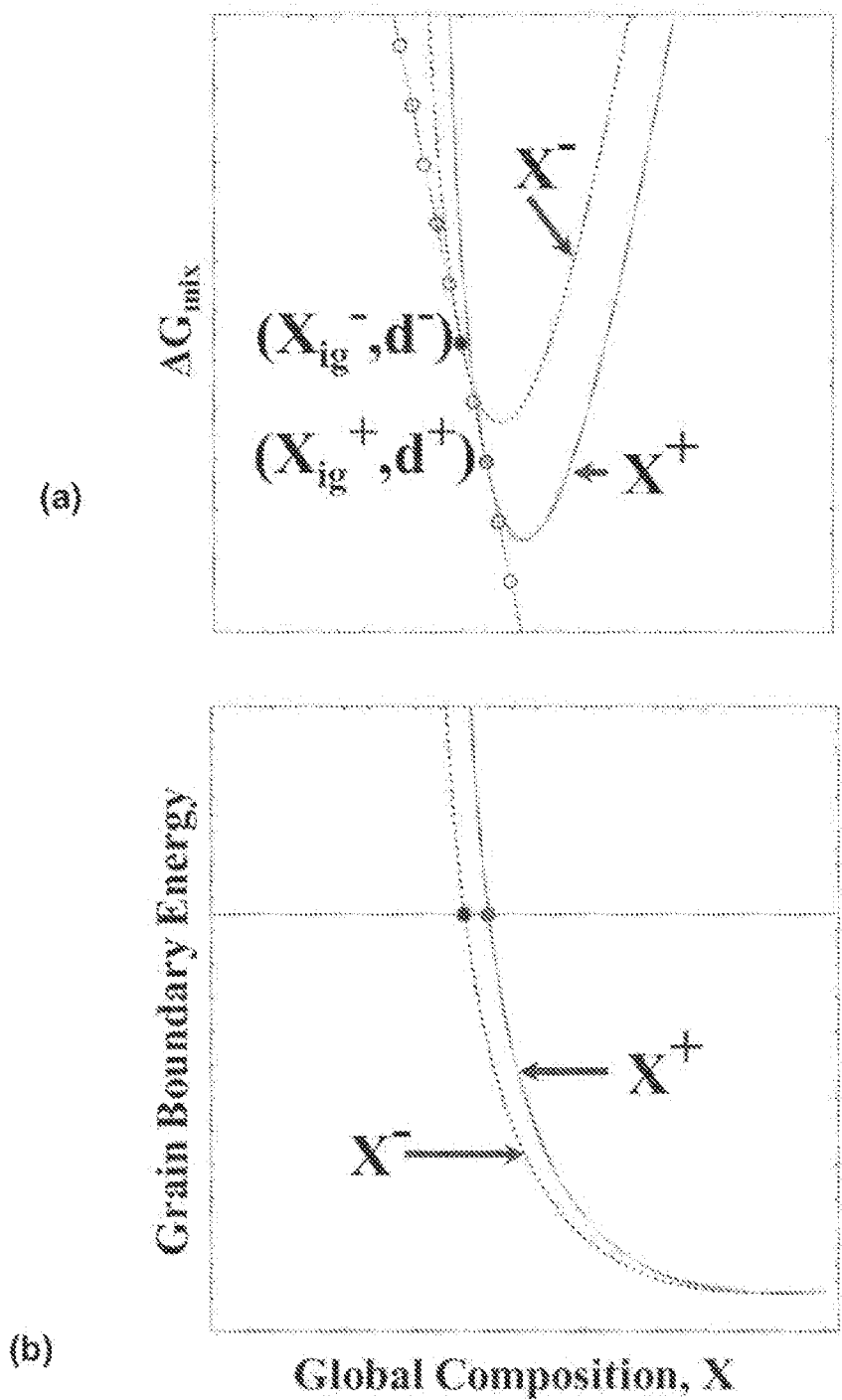
FIGS. 4(a)-4(b) illustrate relationships between free energy of mixing and grain boundary energy, respectively, as a function of global composition, X.

These trends may also be examined on other axes if the variation in free energy are plotted with respect to global composition, X, for a fixed pair of $X_{ig}$ and d (FIG. 4). As seen in FIG. 4, there is a sharp increase in free energy upon moving to the left, and the free energy decrease is obtained by decreasing grain size to a new free-energy curve (with different values of $X_{ig}$ and d). Blue points in FIG. 4(a) represent the minimum in the free energy surface at each value of global composition. For the values of $X^-$ (black dashed) and $X^+$ (magenta), the values of grain size and the grain boundary solute content that comprise the minimum for that global composition are held constant while the global composition is varied. The blue line shows that the minimum points are the tangents between set $X_{ig}/d$ value curves. FIG. 4(b) shows grain boundary energy as a function of global composition for the $X_{ig}$ and d values for the same two minima as denoted in FIG. 4(a) and FIG. 3.

In this embodiment, the shapes of the free energy curves in FIG. 4 are such that they are connected by a common tangent (blue line, FIG. 4) between curves at set values of $X_{ig}$ and d. The common tangent indicates that the system prefers to exist at the combination of grain size and grain boundary solute content that is the minimum of a free energy surface for a given global composition (blue circle).

Based on the aforedescribed explanation, nanocrystalline alloys in an equilibrium grain boundary segregation state may be described in the following way according to one embodiment: the minimum of the free energy surface at each global composition may be treated as a "stoichiometric line compound," represented by a point. In other words, for each composition X, there is one preferred "compound" with a given intergranular concentration and grain size, $(X_{ig}^-, d^-)$. If the global composition is changed, there is a different preferred combination $(X_{ig}^+, d^+)$, and the system resembles a different "compound." When free energy curves are plotted against X, as is traditional in the development of binary phase diagrams, then these points may be compared to the free energy functions of other competing phases.

Figure 5:
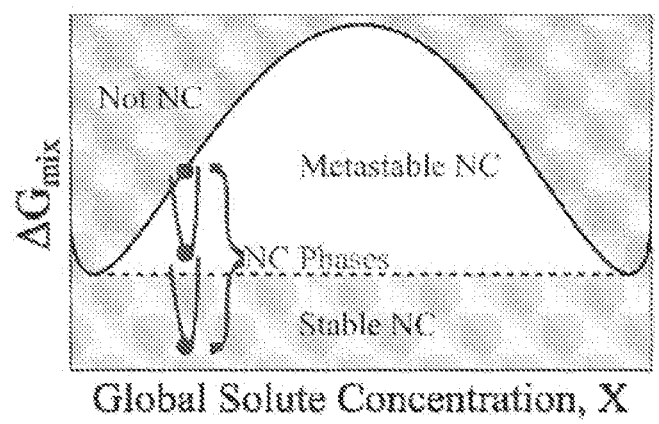
FIG. 5 shows that the free energy of the nanocrystalline (NC) phases (blue) can fall into three regions that are determined by the bulk regular solution (black curve) for the same materials parameters. If there is no minimum in the free energy surface, it is "Not NC". If the free energy surface has a minimum, but its free energy falls above the common tangent of the bulk system (denoting phase seperation, dashed black line), it is "Metasable." A "Stable" nanocrystalline system falls below the common tangent.

FIG. 5 illustrates the comparison between the minimum-energy nanocrystalline system free energy curve and those of competing phases. The competing phases may be, for example, classical bulk (i.e., non-nanocrystalline) phases. The results of the comparison may vary depending on the type of alloy system. For example, the alloy systems described herein may have a positive heat of mixing (or "enthalpy of mixing") or a negative heat of mixing. In one embodiment, the alloy system described herein has a positive enthalpy of mixing. A schematic free energy curve for such a bulk system at a single finite temperature is shown by the solid black line in FIG. 5. This curve is that for a classical phase-separating solid solution, with the two phase field lying between the tangent points of the common tangent line (dashed black line).

This curve, and the two phases represented by it, may be compared to the narrow U-shaped curve associated with a specific nanocrystalline state, as shown schematically by the blue curves in FIG. 5. More specifically, as described above, in some embodiments the nanocrystalline state (or phase) is viewed as a "compound" at a specific point, denoted explicitly by a blue solid point in FIG. 5. Depending upon the specific input parameters used, the location of this point may fall into one of three main regions that are delineated in FIG. 5; "stable nanocrystalline," "metastable nanocrystalline," and "nanocrystalline not supported." Those with minima at a free energy lower than the common tangent of the bulk regular solution limit are labeled as "stable nanocrystalline"; those where the minimum of the free energy surface is the trivial case of infinite grain size and the same free energy of the bulk (non-nanostructured) solid solution occupy the "nanocrystalline not supported" region. Nanocrystalline phases that have a free energy lower than the bulk free energy curve, but higher than its common tangent are labeled as "metastable nanocrystalline." In this latter case, the nanocrystalline structure is more energetically favorable than the single phase solid solution at that solute content, but less favorable than macroscopic phase separation of the system into two solid solutions.

In some embodiments, only positive values for the grain-wise interaction parameter, $\omega g$, that correspond to enthalpies of mixing (Eq. (6)) are employed. Note that the values of this parameter may be negative as well. The parameters may be of any value, such as between about 1 and about 2000 kJ/mol—e.g., about 1 and about 1000 kJ/mol.

In one embodiment, the combination of grain boundary energy and atomic volume divided by the grain boundary thickness to provide a parameter, $\Omega\gamma/t$, of the two pure solvent and solute species may be set to be equal; in the free energy equation, the terms containing these parameters are generally on the order of a tenth the magnitude of the other terms, and less when they appear together as a difference. In some embodiments, term $\Omega\gamma/t$ may be defined to have a value of 8.25 J/mol for both solvent and solute species, but any other value may be selected, depending on the system; for example, the values of $\Omega\gamma/t$ for some common metals are Aluminum: 6.46, Gold: 7.7, Copper: 8.87, Iron: 10.6, and Nickel: 11.5 J/mol. The value of 8.25 J/mol corresponds, for example, to a grain boundary energy of 0.5 J/m$^2$, an atomic volume of 8.25 cm$^3$/mol, and a grain boundary thickness of 0.5 nm.

The variable $\omega_{ig}$ describes the character of atomic interactions in the intergrainular and transition regions (FIG. 1). In general, the grain boundary interaction parameter will be different from the grain interaction parameter. Not to be bound by any theory, but this is the driving force for grain boundary segregation, as the enthalpy of segregation is:

$$\Delta H_{seg} = z\left[\omega_g - \omega_{ig}\left(1 - \frac{v}{1-f_{ig}}\right) - \frac{1}{zI}(\Omega\gamma_B - \Omega\gamma_A)\left(1 - \frac{v}{1-f_{ig}}\right)\right] + \qquad (9)$$
$$2zX_{ig}\omega_{ig}\left(1 - \frac{v}{1-f_{ig}}\right) - 2z[X_g\omega_g + v(X_{ig} - X_g)\omega_{ig}],$$

which comes from the segregation isotherm that emerges fern the RNS model;

$$\frac{X_{ig}}{1-X_{ig}} = \frac{X_g}{1-X_g}\exp\left[\frac{\Delta H_{seg}}{kT}\right]. \qquad (10)$$

Note that the convention is a positive value for the enthalpy of segregation for a system in which the solute preferentially segregates to the grain boundaries. If the segregation enthalpy in Eq. (9) is taken to the dilute limit:

$$\Delta H_{seg}^0 = z\left(\omega_g - \frac{\omega_{ig}}{2} - \frac{(\Omega\gamma_B - \Omega\gamma_A)}{2zI}\right) \qquad (11a)$$

a relationship is obtained between the parameters described herein and a dilute heat of segregation for "enthalpy of segregation"), which is a measurable (or estimable) quantity. In some embodiments, an assumption of $\gamma_A = \gamma_B$ may be employed to reduce the equation further to:

$$\Delta H_{seg}^o = z\left(\omega_g - \frac{\omega_{ig}}{2}\right). \qquad (11b)$$

The grain boundary interaction parameter may be varied to give an enthalpy of segregation, $\Delta H^o_{seg}$ between 1 and 200 kJ/mol. Depending on the system, other values may also be obtained. Given the other values for the parameters appearing in Eq. (11), this means that $\omega_{ig}$ can take on values both positive and negative. Depending on the magnitude of $\omega_g$, a strongly segregating system would have either a positive grain boundary interaction parameter of significantly less magnitude than $\omega_g$ or a negative grain boundary interaction parameter.

The thermodynamic parameters described herein may be a function of temperature; thus the values thereof may vary with the temperature at which they are measured. The temperature may be predetermined at any suitable values. For example, the temperature may be about 1700 K, 1600 K, 1500 K, 1400 K, 1300 K, 1200 K, 1100 K, 1000 K, 900 K, 800 K, 700 K, 600 K, 500 K, 400 K, 300 K, $0.35 T_{cr}$, $0.5 T_{cr}$, $0.65 T_{cr}$, $0.85 T_{cr}$, where $T_{cr}$ is the critical temperature defined at the top of the miscibility gap as aforedescribed and may be related to other parameters by the relationship ($T_{cr}=z\ \omega_g/2R$). The temperature may be any other suitable temperatures.

The systems and methods described herein allow the two interaction parameters to be varied at high resolution (down to intervals of 0.001 eV) across the ranges described above, and the minimum free energy curves for multiple compositions to be calculated across the full range of compositions (X=0 to 1). As shown below, the free energy curves for over 100 compositions were calculated. These minima are plotted against the bulk regular solution free energy curve with the same values of $\omega g$ and z (as in FIG. 5).

Nanocrystalline Stability Map

One feature of the presently described models is that it may provide an article that may contain a diagram showing a map of stability associated nanocrystalline phase; in some embodiments herein the diagram is referred to as a "nanocrystalline stability map." The diagram may take any form. FIGS. 11-14 provide examples of such diagrams in some embodiments, which are discussed further below. As shown in the figures, the diagram may delineate a plurality of regions respectively representing different stable phases of at least one binary alloy. The different phases may be any of the phases described above. In some embodiments, the respective regions of the plurality of regions are delineated by at least one boundary determined as a function of at least two thermodynamic parameters associated with grain growth and phase separation of the at least one binary alloy.

While the construction of the map is described in a later section, the different regions of the map in one embodiment are described below.

Non-Nanocrystalline (No Stability)

In some embodiments, there may be two cases in which a system has no stable nanocrystalline configuration. The first case may occur when there is no free energy curve with a minimum at a finite grain size for any of the possible compositions. FIG. 2(b) depicts this situation. This situation may arise in cases where the heat of segregation is insufficiently large with respect to the value of the heat of mixing, and as a result, no energy minimum exists over the entire range of composition because the alloying interactions in the grain boundary are not sufficiently different from those in the grains to drive solute segregation.

The second case may occur for systems that have nanocrystalline energy minima across a wide range of compositions (and energies either stable or metastable with respect to phase separation) but still have composition ranges where the nanocrystalline state is not stable. For example, when the global composition is below the solubility limit, no stable nanocrystalline compounds are identified. In other words, in phase separating alloys, supersaturated solid solutions are needed to achieve a nanocrystalline structure stable against grain growth. Note that some of the prior analytical, models of segregation in nanocrystalline systems, such as those by Weismuller and Kirchheim, are developed with the assumption of a dilute limit. The model described herein shows that such an assumption may be problematic for alloys with positive heats of mixing, and non-dilute solubility limits, as in at least some of the alloy systems provided herein. The models described here do not suffer such a deficiency.

Stable Nanocrystalline

Figure 11:
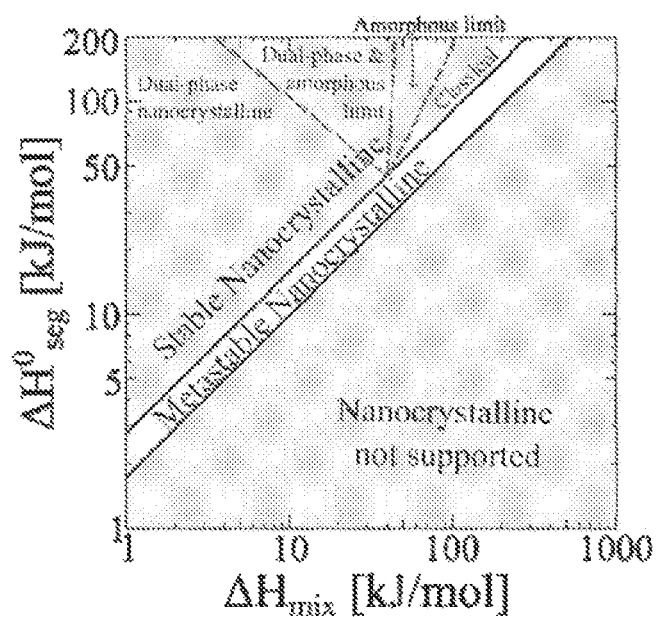
FIG. 11 shows a nanocrystalline stability map according to one embodiment, showing delineated regions of stability (green), metastability (yellow), and no stability (red) in binary alloys as a function of their enthalpies of mixing and segregation.

The types of nanostructures that are thermodynamically stable may be diverse. Accordingly, as shown in FIG. 11, the stable nanocrystalline phase may be further divided into sub-regions. In some embodiments, the stable phase may include at least one of dual-phase nanocrystalline, dual-phase nanocrystalline and amorphous phase; amorphous phase; and a classical segregation-stabilized nanocrystalline phase as depleted in a nanocrystalline stability map.

Classical Segregation-Stabilized Nanocrystalline Region

In some embodiments, for some combinations of high heats of mixing and high heats of segregation, the condition of segregation-based nanostructure stabilization envisioned by Weissmuller may be achieved. In these cases the relationship between the enthalpies is such that the grain boundary interaction parameter approaches ideal behavior, namely $\omega_{ig}=0$.

Figure 6:
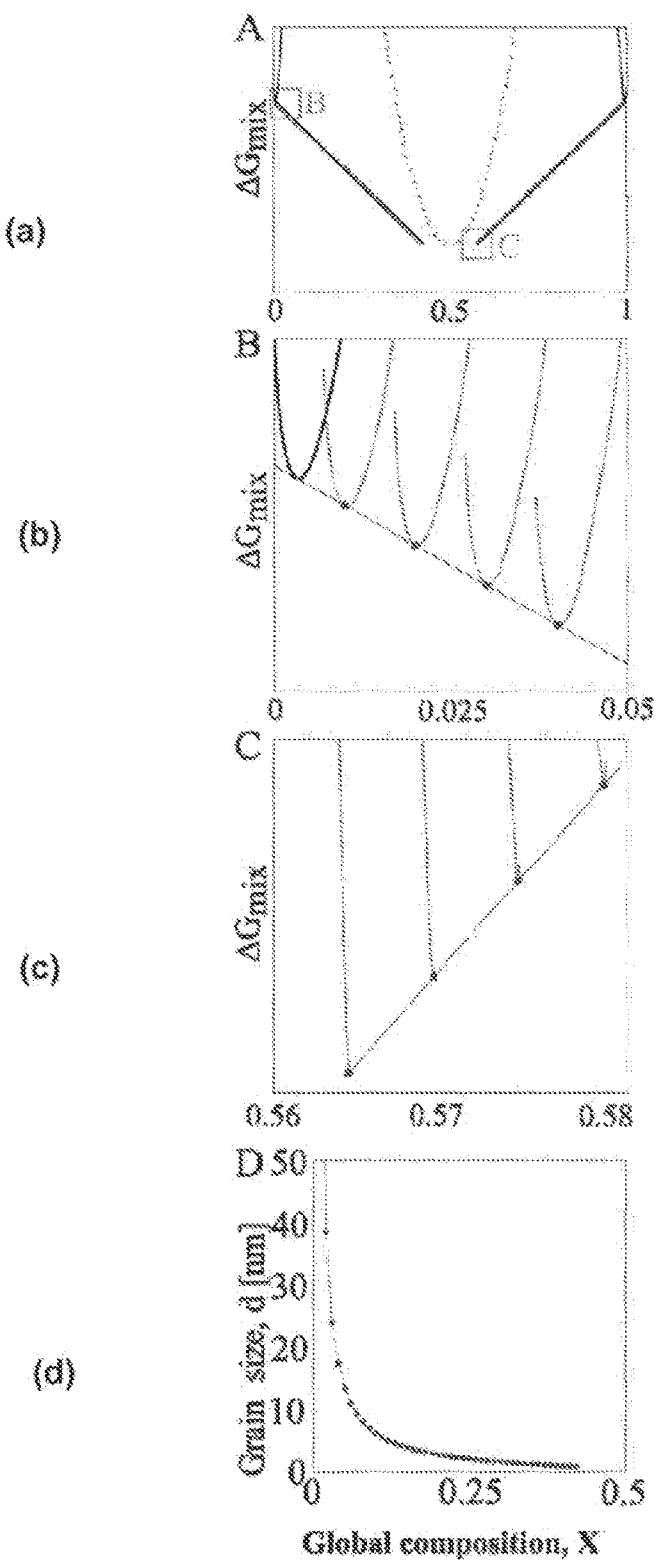
FIGS. 6(a)-6(d) show: (a) free energy comparison of regular solution (black curve), amorphous phase limit (green dashed curve), and the nanocrystalline points (blue circles) for the "classical nanocrystalline" case; (b) an enlarged view of the free energy comparison of nanocrystalline points as they approach the regular solution at the solubility limit, in the region marked in (a); (c) an enlarged scale free energy comparison of the terminus of the nanocrystalline points as indicated by the box in (a)—the final composition that supports a nanocrystalline phase due to the ($X_{ig}$, d) space limitation is seen with respect to global composition; (d) grain size versus global composition.

A representative free energy curve comparison in one embodiment is provided in FIG. 6(a). Each blue point in the figure represents a nanocrystalline "compound." FIG. 6(a) shows free energy comparison of regular solution (black curve), amorphous phase (green dashed curve), and the nanocrystalline points (blue circles) for the "classical nanocrystalline" case; this example case has a non-limiting exemplary enthalpy of mixing of 81 kJ/mol and enthalpy of segregation of 79 kJ/mol.

In the magnified views of FIGS. 6(b) and 6(c), the local free-energy curves corresponding to a few such points are illustrated; the points corresponding to the stable condition all lie on a single common tangent line. The points shown are only examples, and there are in fact an infinite number of them between any two of those shown; the locus of the points represents a smooth continuum of stable grain sizes that are a monotonic function of the composition. In one embodiment, the grain size decreases with increasing solute content in the relationship often observed in experimental systems. See FIG. 6(d).

In some embodiments, there is a well-defined composition range with clear upper and lower bounds or limits with respect to solute concentration, over which a nanocrystalline phase is stable. The limits and thus the boundaries set by the limits across a range of parameters as shown on a stability map may be determined by a plurality of thermodynamic parameters, such as those described above. For example, at low solute concentrations, the existence of nanocrystalline phase is bounded by the solubility limit, below which so nanocrystalline minima exist. This is already discussed above and may be seen graphically in the magnified view of FIG. 6(b). For high solute concentrations, the limiting composition may be seen based on Eq. (2). For a given global composition, there is a limit to the ($X_{ig}$, d) combinations that may be supported while conforming to Eq. (2); if all of the solute is present in the grain boundaries and none in the grain interiors, $X=f_{ig}X_{ig}$ restricts the smallest grain size and largest value of solute allowable for a stable nanocrystalline phase. This limitation may create boundaries on the free energy surface, beyond which no surface exists. See e.g. FIG. 2(a) (on the left-hand side where the smallest grain sizes cannot be accessed on the free energy surface). This truncation of the free energy curves can also be seen in the magnified view in FIG. 6(c), which shows the points for the nanocrystalline states close to the limiting composition, as well as their individual free energy curves; note that these are all truncated on the left-hand side, at the limits achievable by Eq. (2). The truncation becomes more pronounced as the concentration rises, and the last nanocrystalline compound—that with the largest possible solute content—is the last that has a minimum in the free energy surface contained within the available range of grain size and solute distribution (FIG. 6(c)). In one embodiment, this compound may be referred to as the "terminal" nanocrystalline structure.

The series of blue points that all lie on a common "nanocrystal free energy line" are a common feature of many systems, and the arrangement of these lines in the free energy diagram may lead to several possible situations. In the case pictured in FIG. 6(a), for example, these lines end at the terminal nanocrystalline structure, leaving a gap between their ends. These terminal structures have the lowest free energy in the system, far lower than that of the bulk regular solution. The nanocrystalline phases in this system are also in equilibrium with the bulk regular solution phase. For non-dilute alloys, there is a miscibility gap that separates the terminal solvent-rich nanocrystalline compound and its counterpart terminal solute-rich nanocrystalline compound. In some embodiments, these nanocrystalline compounds are symmetric, due to the assumption of equal $\Omega\gamma/t$ for solvent and solute. As noted above, different assumptions, and thus different shapes of the graphs for the nanocrystalline compounds may exist.

For the exemplary system presented in this figure, another apparent "phase" is observed, shown by the green dashed line in FIG. 6(a). This free energy curve corresponds to the intergranular regular solution (Eq. (8))—the limit of the RNS model as grain size, d, approaches the grain boundary width, t (i.e., as the system approaches the "amorphous limit" where the material is entirely composed of intergranular state). The situation may arise where the amorphous limit can be lower in energy in the central composition region where nanocrystalline states are not supported due to the ($X_{ig}$, d)-space limitations.

For these cases in the classical region, this may lead to equilibrium between the terminal nanocrystalline compound and the amorphous limit phase (similarly, between the amorphous limit phase and the right hand terminal nanocrystalline compound). The case where the amorphous limit exhibits a lower free energy than the nanocrystalline points such that it forms the lowest common tangent with the bulk regular solution is discussed in the following section.

Amorphous Phase

Figure 7:
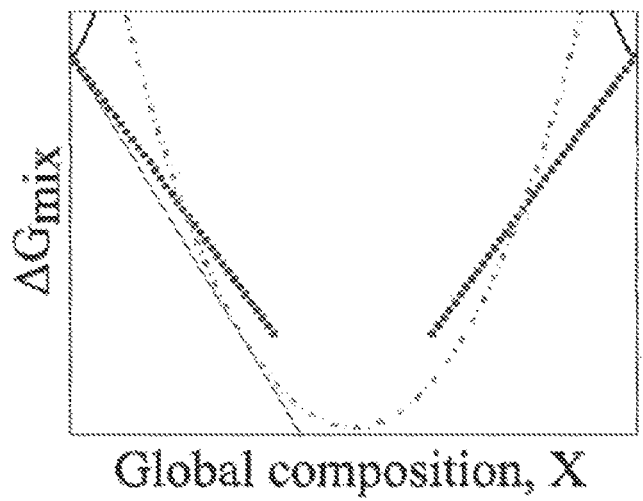
FIG. 7 illustrates that the free energy of the amorphous phase (green dashed curve) is lower than that of the bulk regular solution (black curve) and the nanocrystalline points (blue circles).

In some embodiments, the "intergranular phase" described above has the lowest free energy curve, as shown in FIG. 7 in one embodiment, where this curve falls below the free lines of the nanocrystalline structures. This example case has a non-limiting exemplary enthalpy of mixing of 93 kJ/mol and enthalpy of segregation of 104 kJ/mol. This situation may arise when the grain boundary interaction parameter is negative and the grain interaction parameter positive; this drives the preference for intergranular regions over crystalline ones. That the intergranular term of the RNS could in fact have the lowest free energy of any other possible state suggests that there are positive heat of mixing systems in which an "amorphous" state is stable (due to its relatively lower heat of mixing). As shown in FIG. 7, when the intergranular phase is the lowest free energy state, it is in equilibrium with the bulk regular solution. Not to be bound by any particular theory, but this may be related to a common metric for assessing binary amorphous systems: the Glass forming Range ("GFR"). There are a number of approaches to estimate the GFR (i.e., size/structure difference, eutectic shape, and enthalpy models) and the model described herein provides an alternative.

Dual-Phase Nanocrystalline

Figure 8:
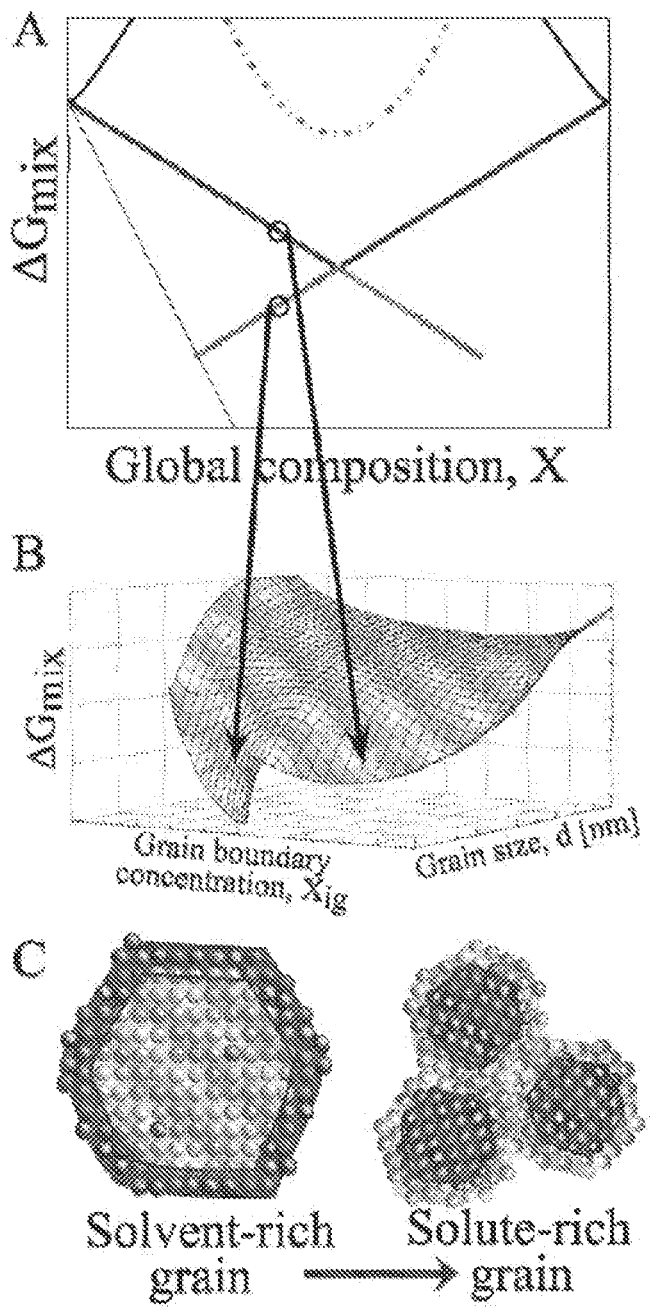
FIGS. 8(a)-8(c) show: (a) free energy plot showing regular solution (black curve), nanocrystalline phases with solute rich grain boundaries (blue circles), and nanocrystalline phases where the solvent has become the grain boundary element (red diamonds); (b) free energy surface for a given global solute composition showing the two minima; (c) schematic of the nanostructure rearrangement from solvent rich grains to solute rich grains.

In some embodiments, when the heat of segregation is larger than the heat of mixing, such that $\omega_{ig}$ is negative, but not sufficient to drive the system to the amorphous limit, the free energy surface at a given composition (FIG. 8(b)) supports two minima where the grain boundary energy is zero; hence the designation "dual-phase nanocrystalline." FIG. 8(a) shows free energy plot showing regular solution (black curve), nanocrystalline phases with solute rich grain boundaries (blue circles),and nanocrystalline phases where the solvent has become the grain boundary element (red diamonds); this example has a non-limiting exemplary enthalpy of mixing of 23 kJ/mol and enthalpy of segregation of 35 kJ/mol. One of these minima is the classic grain boundary segregation-stabilized state (i.e., the solute is strongly segregated to the grain boundaries, and the stabilized grain size continues to decrease with an increase in composition along the nanocrystal free energy line). The second minimum has solute-rich grains with the solvent segregated to the grain boundary. Because $\omega_{ig}$ also describes the cross-interactions between the crystalline and intergrainular regions (see FIG. 1), a mildly negative value of this parameter may lead the system to maximize unlike bonds crossing between these regions. This in turn may promote a finer grain size, and in order to support the increased grain boundary volume, the intergranular region must be occupied by the solvent element. Thus, the roles of solute and solvent are exchanged and the preferred system becomes a "solute nanocrystalline phase." The composition range of such solute nanocrystalline phases is limited by the same ($X_{ig}$, d)-space constraints as the classical "solvent" nanocrystalline phases. In some embodiments, the solute nanocrystalline phases may also follow a composition-grain size relationship; however, as the solute concentration decreases from the equiatomic concentration, the grain size decreases.

While this case is described as "dual-phase nanocrystalline" due to the existence of two nanocrystalline phases stable against grain growth at a single composition, the solute nanocrystalline phase is lower in free energy. Constructing common tangents on FIG. 8 may lead to a conclusion that over a broad range of compositions the solute nanocrystalline phase is in equilibrium with the bulk regular solution; on the solvent rich side of the phase diagram, the stable states are a solvent rich solid solution and a solute rich nanocrystalline phase with grain boundary segregation. In the middle of the diagram, the equilibrium is between two solute nanocrystalline phases, which should be an interesting dual-phase nanocomposite that would in general be a true stable bimodal structure.

Dual-Phase Nanocrystalline/Amorphous Structures

Figure 9:
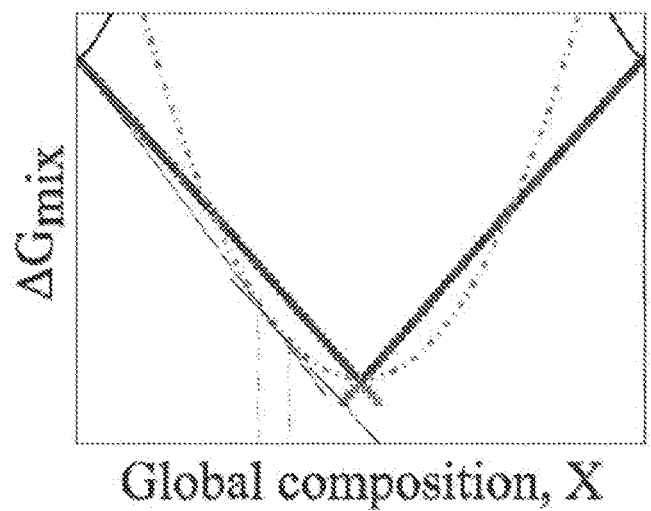
FIG. 9 shows a free energy plot for a case where the amorphous limit (green dashed curve) appears below the common tangent (thin black line) between the regular solution (thick black curve) and nanocrystalline phases (solvent nanocrystalline phases in blue; solute nanocrystalline phases in red diamonds).

The cases where the nanocrystalline points compete with an amorphous phase, or with one another (solute nanocrystalline phase), have been provided above. These cases correspond to a relatively higher and lower heat of mixing, respectively. Between these two cases may be a condition in which both the intergranular free energy curve (amorphous limit) and the terminal compositions of the nanocrystalline free energy lines are stable. An example of this situation is shown in FIG. 9, where the low energy of the intergrainular regions places it in equilibrium with the bulk regular solution at low solute levels. This example is a non-limiting, exemplary enthalpy of mixing of 58 kJ/mol and enthalpy of segregation of 75 kJ/mol. At higher concentrations, the amorphous limit is in equilibrium with the solute nanocrystalline phase defined by the terminal structures of the nanocrystal free energy lines. The two solute nanocrystalline phases are in equilibrium around the equiatomic composition.

Metastable Nanocrystalline Alloys

Figure 10:
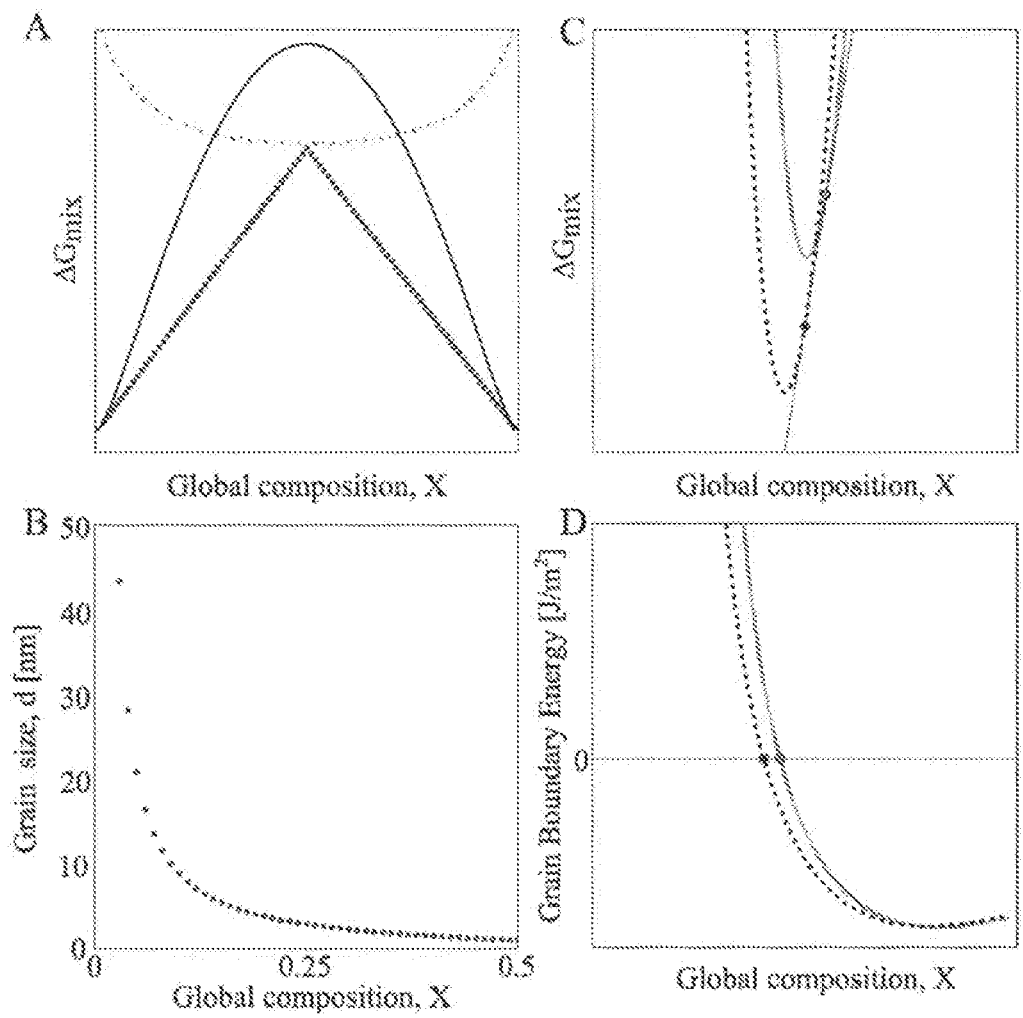
FIGS. 10(a)-10(d) show: (a) a free energy comparison of regular solution (black curve) and nanocrystalline points (blue circles); (b) grain size as a function of the global solute concentration in a metastable nanocrystalline binary alloy; (c) similar to FIG. 4, the minima for two compositions are plotted as points, while the curves represent the free energy as a function of composition if the $X_{ig}$ and d values for those minima are held constant; (d) grain boundary energy as a function of global composition for the $X_{ig}$ and d values for the same two minima as denoted in (a).

In some embodiments, the stable phase is a metastable nanocrystalline structure. In the case of metastable nanocrystalline structures, the RNS model may exhibit a minimum energy in the d–X space, and grain size may decrease with composition in a relationship similar to other model predictions and experimental data. However, these states may be unstable with respect to macroscopic phase separation into the bulk phases. FIG. 10(a) depicts the free energy diagram of such a system in one embodiment, which system contains nanocrystalline free energy lines that lie below the regular solution free energy curve, but above the common tangent denoting bulk phase separation (the yellow region of FIG. 5). This example has a non-limiting exemplary of mixing of 58 kJ/mol and enthalpy of segregation of 49 kJ/mol. A nanocrystalline system in this condition would be stable against grain growth but would lower its energy via phase separation on the bulk scale.

However, the situation surrounding the free energy minima in this case is not quite the same as seen in the earlier analysis using $X^+$ and $X^-$ for the case of a stable nanocrystalline structure. In that case, decreasing the composition at the set values of $X_{ig}$ and d resulted in a sharp increase, and increasing the composition led to a lowering of the free energy through decreasing grain size. In the metastable case, the same types of behavior are seen, but with opposite composition tendencies (FIG. 10(c)-10(d)). For an increase in composition, the free energy increases rapidly; for a decrease in composition, the grain boundary energy is positive, and as a result the system favors grain growth. This pattern continues until the infinite grain size of the regular solution is obtained. (FIG. 10(b)). At the nanocrystalline compound values of $X_{ig}$ and d the grain boundary energy is reduced to zero, reducing the drive for grain growth, but the free energy of a system with a larger grain size may be a lower free energy state. At the same time, the lower free-energy of the common-tangent bulk phases may favor phase separation in the structure, such that the equilibrium structure becomes a coarse-grained, phase separated system.

Applications

The aforedescribed methods and models may be employed to identify the stable phase of an alloy; in some embodiments the alloy is a binary alloy. For example, the methods and models described herein may be able to identify whether a binary alloy would be stable as a nanocrystalline alloy (or in a nanocrystalline phase). Further, by using certain thermodynamic parameters, the presently described methods and models allow identification of any binary alloy that may be stable (against both grain growth and phase separation) as a nanocrystalline alloy. The methods and models described herein are versatile and may be applicable to any types of alloys. Including alloys that have a face-centered cubic (FCC), body-centered cubic (BCC), or hexagonal closed-packed (HCP) lattice arrangement. Also, any of the steps in the model described herein may be repeated for a plurality of binary alloys.

By using the methods, systems, and articles provided herein, binary alloys that may be stable as a stable nanocrystalline alloy may be identified. Once an alloy that is identified as one that may be stable as a nanocrystalline alloy, the alloy may be fabricated. Any fabrication technique suitable for the particular alloy may be employed. For example, the technique may be electrodeposition, (physical or chemical), vapor deposition, plasma spraying, mechanical, alloying and other powder-based production routes, casting or solidification, etc.

As described in the section below, a nanocrystalline stability map may be constructed by determining the boundaries of the stability regions and then compared the thermodynamic parameters of a binary alloy against the boundaries to determine the stable phase of the binary alloy—stable nanocrystalline, metastable nanocrystalline, or non-nanocrystalline. In other words, by comparing the thermodynamic parameters of a binary alloy against predetermined values (i.e., the boundaries), the stable phase of the binary alloy may be identified.

The generation and population of data points into the nanocrystalline stability map may be automated. For example, the method can be automated by a software program executable by an information processor, such as a computer. The information processor may be a part of a system that includes (i) at least one memory storing processor-executable instructions and (ii) at least one information processor coupled to the at least one memory, wherein upon execution of the processor-executable instructions the processor implements the methods described herein. In some embodiments, the system includes a computer, which includes a processor connected to a bus. Input/output (I/O) devices are also connected to the bus, and can include a keyboard, mouse, display, and the like. An executable program including a set of processor-executable instructions for identifying stable binary alloy phases as described above is stored in memory, which is also connected to the bus. In one embodiment, a program that can execute the presently claimed methods is recorded on a non-transitory computer-readable recording medium, such as a compact disc (CD), floppy diskette, or DVD.

NON-LIMITING WORKING EXAMPLE

Example 1

Nanocrystalline Stability Map

The above discussions delineated the types of behavior that emerge from the RNS model for positive heats of mixing; which of these situations is relevant for a given alloy system depends principally upon its mixing parameters (in the grains and intergranular region). Through the thousands of individual calculations conducted here, we were able to delineate regimes in the mixing-parameter space corresponding to each behavior described above. These regions of stability are plotted (FIG. 11), using as axes the enthalpies of mixing (Eq. 6) and segregation (Eq. 11).

It was found that the regions separating stability, metastability, or unsuitability of a nanostructured alloy system are demarcated by straight lines in the double-logarithmic space of FIG. 11. While these lines are not of slope unity, they correspond to a power-law, and can be empirically captured by Eq. (12):

$$\frac{\Delta H_{seg}}{\Delta H_{mix}^a} = c,$$

where a is the power-law slope, and c reflects the intercepts. Both of these are in general a function of temperature; for the map presented in FIG. 11, $T=0.35\ T_{cr}$. They may be obtained by fitting a certain number of data points. For other temperatures investigated thus far (see Table 1), the map has the same basic form, but with shifted boundaries reflected in the different fitted values of a and c.

TABLE 1

Coefficients for the Nanostructuring figure of merit, Eq. (12) at three temperatures, as a function of the critical temperature

| Temperature | a (slope) | c (intercepts) Metastable | c (intercepts) Stable |
|---|---|---|---|
| 0.35 $T_{cr}$ | 0.757 | 1.7326 | 2.768 |
| 0.5 $T_{cr}$ | 0.661 | 2.8038 | 3.7236 |
| 0.65 $T_{cr}$ | 0.567 | 4.425 | 4.958 |

At the highest level, the map in FIG. 11 snows the trade-off between grain boundary and bulk segregation tendencies as controlling the ability to stabilize a nanocrystalline phase. In fact, the power-law-modified ratio of the two quantities collected on the left-hand side of Eq. (12), $\Delta H_{seg}/\Delta H_{mix}^a$, represents a useful figure of merit for binary systems' nanostructuring ability, with higher values lying more towards the upper-left of the stability map.

Example 2

Construction of Nanocrystalline Stability Map

The boundary of the stable phase region on the map for a nanocrystalline alloy may be determined by the relationship:

$$\frac{\Delta H_{seg}}{\Delta H_{mix}^a} = c, \quad (12)$$

wherein $\Delta H_{mix}$ and $\Delta H_{seg}$ each independently represents an enthalpy of mixing and an enthalpy of segregation (or "segregation enthalpy") of a particular alloy system; a and c are temperature dependent constants and each independently represents a slope and an intercept of each of the boundary line.

The enthalpy of mixing used in the RNS calculations is that of a regular binary solution, $$\Delta H_{mix} = z\omega_g X(1-X), \quad (13)$$

where z is the coordination number and ω is the interaction parameter describing the tendency of atoms to phase separate or order, based on the energies associated with like and dislike atomic bonds:

$$\omega = E^{AB} - \frac{E^{AA} + E^{BB}}{2}, \quad (14)$$

wherein the subscript g on the interaction parameter in the enthalpy of mixing denotes that the interactions described are those in the grain interior (or if the material were single crystalline, the bulk). Eq. (14) is the same as Eq. (5) above. The segregation enthalpy for this work is an interplay between the interactions in the grain interior and those of the grain boundary, or intergranular (ig) region:

$$\Delta H_{seg}^0 = z\left(\omega_g - \frac{\omega_{ig}}{2}\right). \quad (15)$$

In one embodiment, Equation (16) arises from the assumption of equal grain boundary energies/atomic volume combination, Ωγ/t for solute and solvent content when constructing the stability map and associated figure of merit.

Enthalpy of Mixing

There are many ways to calculate the enthalpy of mixing for a wide range of alloys for the construction of the stability map. For example, one may use thermodynamic analytical models, ab initio computer simulations, atomistic computer simulations, thermodynamic software, phase diagram information, direct experimental measurements by, e.g., calorimetry, grain boundary chemical analysis, etc.; any of these methods may be used in connection with the present inventions. For example, an analytical model like the Miedema model may be employed for the determination of the enthalpy of formation of a concentrated (i.e. not dilute) solid solution:

$$\Delta H_{s.s}^{form} = \Delta H_{s.s}^{chemical} + \Delta H_{s.s}^{elastic} + \Delta H_{s.s}^{structural}. \quad (16)$$

The expression contains three terms that describe the chemical, elastic, and structural enthalpy changes associated with a solid solution of two atomic species. The structural term was found by Miedema and others to be negligible (±1 kJ/mol, and only if both species are transition metals), therefore we omit this term in our calculations. The contributions to the chemical and elastic terms are summarized in Table 2.

TABLE 2

Miedema Enthalpy of Mixing Terms

| | |
|---|---|
| $V_A, V_B$ | molar volume |
| $c_A, c_B$ | Concentration |
| $c_A^s, c_B^s$ | surface fraction |
| K | bulk modulus |
| G | shear modulus |
| $\psi_A, \psi_B$ | work function for electron transfer |
| $n_{ws}^A, n_{ws}^B$ | electron density at boundary of Wigner-Seitz cell |
| P, Q | constants |
| $W_A, W_B$ | spherical volume of an atom or hole |

$$\Delta H_{s.s.}^{chemical} = c_A c_B (c_B^s \Delta H_{AinB}^{inter} + c_A^s \Delta H_{BinA}^{inter})$$

$$\Delta H_{AinB}^{inter} = \frac{(V_A)^{2/3}}{\frac{1}{2}\left(\frac{1}{n_{ws}^{A\,1/3}} + \frac{1}{n_{ws}^{B\,1/3}}\right)}\left\{-P(\Delta\psi)^2 + Q\left(\Delta n_{ws}^{\frac{1}{3}}\right)^2\right\}$$

$$\Delta H_{BinA}^{inter} = \frac{(V_B)^{2/3}}{\frac{1}{2}\left(\frac{1}{n_{ws}^{A\,1/3}} + \frac{1}{n_{ws}^{B\,1/3}}\right)}\left\{-P(\Delta\psi)^2 + Q\left(\Delta n_{ws}^{\frac{1}{3}}\right)^2\right\}$$

$$c_A^s = \frac{c_A * V_A^{2/3}}{c_A * V_A^{2/3} + c_B * V_B^{2/3}}$$

$$c_B^s = \frac{c_B * V_B^{2/3}}{c_A * V_A^{2/3} + c_B * V_B^{2/3}}$$

$$\Delta H_{s.s}^{elastic} = c_A c_B (c_B \Delta H_{AinB}^{elastic} + c_A \Delta H_{BinA}^{elastic})$$

$$\Delta H_{AinB}^{elastic} = \frac{2 * K_A * G_B * (W_A - W_B)^2}{3 * K_A * W_B + 4 * G_B * W_A}$$

$$\Delta H_{BinA}^{elastic} = \frac{2 * K_B * G_A * (W_A - W_B)^2}{3 * K_B * W_A + 4 * G_A * W_B}$$

$$W_A = \left(V_A + \alpha * \frac{(\psi_A - \psi_B)}{n_{ws}^A}\right)$$

TABLE 2-continued

Miedema Enthalpy of Mixing Terms $$W_B = \left(V_B + \alpha * \frac{(\psi_A - \psi_B)}{n_{ws}^B}\right)$$

$$\alpha = 1.5 * \frac{(V_A)^{2/3}}{\frac{1}{n_{ws}^{A\,1/3}} + \frac{1}{n_{ws}^{B\,1/3}}}$$

$$\alpha = 1.5 * \frac{(V_B)^{2/3}}{\frac{1}{n_{ws}^{A\,1/3}} + \frac{1}{n_{ws}^{B\,1/3}}}$$

The chemical term includes $\Delta H_{AinB}^{inter}$, which describes the chemical interaction of an A atom completely surrounded by B atoms and the surface faction, $c^8_A$, which describes the adjustment made when the A atom has non-B neighbors. The elastic term makes use of Eshelby's elastic formulism and describes fitting an approximate sphere of one atom in a hole in the matrix of the other species.

The Miedema enthalpy is not in the form of a regular solution; in order to extract the regular solution interaction parameter ($\omega=z\omega$), $\Delta H_{s,s}^{form}$ was calculated across the full range of X and fit to an equation of the form $\Omega X(1-X)$.

While the Miedema model makes a reasonable estimate for a wide range of binary alloys, it can sometimes result in non-physical predictions; for example, the calculated formation enthalpy is negative (indicating an ordering system) while the phase diagram presents a phase-separating miscibility gap.

The next source for a wide range of alloys is the CAL-PHAD method of calculating phase diagrams. Most free energy functions fitted using this method utilize the Redlich-Kister-Muggiano equation for the excess free energy term (enthalpy of mixing):

$$G^{excess} = X_A X_B \sum_i (X_A - X_B)^j L_i(T) \text{ where} \quad (3)$$

$$L_i(T) = A_i + B_i T$$

The full form for the excess term is fit to the regular solution to find the interaction parameter, $\Omega=z\omega$. For RKM coefficients that are temperature dependent, the particular multiple of the critical temperature (describing the top of the miscibility gap in a phase separating system, $T_{cr}=z\omega_g/2R$) being used for the figure of merit constants $\alpha$ and $c$ is used in the calculation; for example T is replaced with $0.35*\Omega/2R$ in the RKM coefficient when calculating the figure of merit for $0.35*T_{cr}$.

Finally, interatomic potentials for atomistic modeling of binary alloys (e.g. EAM) can be used for the enthalpy of mixing. Most often reported in these studies is the dilute mixing enthalpy, the enthalpy associated with one atom of species A, surrounded by atoms of species B. This type of term is analogous to Miedema's $\Delta H_{AinB}^{inter}$; as such, to calculate an enthalpy of mixing for a non-dilute solid solution, it is used in place of $\Delta H_{AinB}^{inter}$ (Table 2) in the chemical term of Eq. (16).

Enthalpy of Segregation

Interfacial segregation is often characterized via the following isotherm relating the composition of the interface, $x_i$, the composition of the bulk, X, and the segregation enthalpy, $\Delta H_{seg}$:

$$\frac{x_i}{1-x_i} = \frac{X}{1-X} \exp\left[-\frac{\Delta H_{seg}}{RT}\right]. \quad (17)$$

The $\Delta H_{seg}$ describes the change in enthalpy associated with exchanging an atom of one species from the bulk with an atom of another species at the interface (the segregating atom is not required to be the minority/solute element). There are three contributions in existing models for the segregation: elastic (the strain energy associated with misfiting atoms), chemical (the interaction energy between the two species of atoms), and interfacial energy (the difference in surface/grain boundary energies of the two species).

The elastic strain energy change can be written using "continuum linear elastic formalism":

$$\Delta E_{el} = \frac{24\pi K_A G_B r_B r_A (r_B - r_A)^2}{3K_A r_A + 4G_B r_B} \quad (18)$$

Solute is denoted by subscript B and solvent by subscript A; K is balk modulus, G is shear modulus, r is the atomic radius. This term is positive, meaning the elastic component always favors segregation.

The difference in interfacial energies, $\gamma$, and the area per mole of the interface, $\sigma=N_{avg} V_B^{2/3}$ is described by the first term of Eq. (19):

$$(\gamma_B - \gamma_A)\sigma + 2\omega\left[z^l(x-x^s)+z^v\left(x-\frac{1}{2}\right)\right]; \quad (19)$$

while the second term describes the chemical interactions; where $\omega$ is the interatomic interaction parameter, the total coordination number of the system, z, is split into in-plane, $z^l$, and out of plane, $z^v$, coordination through the following relation: $z=z^l+2z^v$. The combination of Eq. (18) and Eq. (19) is the Wynblatt-Ku model for interfaced segregation.

These terms were first used to model surface segregation; it has been shown that the elastic term needs no modification to be used in both surface segregation and grain boundary. Darling and coworkers suggest modifications to the Wynblatt-Ku model for use with grain boundaries:

$$\Delta H_{seg} = (\gamma_B - \gamma_A)(1-\alpha)\sigma - \quad (20)$$

$$\frac{8\Delta H_{mix}}{z}\left[z^l(x^s-x) - z^v\left[\left(x-\frac{1}{2}\right) + \alpha\left(x^s-\frac{1}{2}\right)\right]\right] - \Delta E_{el}.$$

The interfacial energy term is modified by a parameter, $\alpha$, which accounts for the ratio between interfacial and surface strengths (arbitrarily chosen in their work as 5/6).

In order to solve for the segregation state, Equation (17) is solved with the model for segregation energy (i.e. Wynblatt-Ku or Eq. (20)). The value of the segregation enthalpy cannot be calculated independently of the composition profile, temperature, or other variables. To make an estimation of the segregation energy separately, without a need for solving equation (17) or making any concentration assumptions, Miedema's model was used for surface segregation calculation:

$$\Delta H_{seg} = 0.71 \cdot \frac{1}{3} \cdot \left[ -\Delta H_{AinB}^{int} - c_0 \gamma_B V_B^{\frac{2}{3}} + c_0 \gamma_A V_A^{\frac{2}{3}} \right]. \quad (21)$$

The chemical interaction term, $\Delta H_{AinB}^{int}$, $\gamma$, and V are defined the same as above; the term $$c_0 \gamma V^{\frac{2}{3}},$$

is the surface enthalpy of a pure metal as defined by Miedema, and $c_0$ is a semi-empirical constant defined as $4.5 \times 10^8$.

The coefficient $$\frac{1}{3}$$

describes the fraction of contact at a surface—when the A atom is at the surface rather than the bulk, it has gone from being surrounded by B atoms to having only $$\frac{2}{3}$$

in contact. With this fractional contact, $$\frac{1}{3}$$

of the interfacial energy is lost $$\left( \frac{1}{3} \Delta H_{AinB}^{int} \right), \frac{1}{3}$$

of the surface that was B is lost, and $$\frac{1}{3}$$

of the surface is now A. The coefficient 0.71 is due to surface relaxation (both of the surface electron density distribution and the geometry of the surface layer). As a result, the fraction of the surface area of a surface layer atom in contact with the vacuum gets smaller than ⅓.

In Eq. (21) both chemical interaction energy, $\Delta H_{AinB}^{int}$, and interfacial energy terms describing the chemical and interfacial driving forces for segregation are mirrored in the previously discussed models for segregation. From the RNS model, v, the fraction of interface atoms contributing to the effective coordination of transitional bonds is taken to be ½. Following the Miedema formulation, an atom in the grain boundary will lose ⅙$^{th}$ of its contact with other atoms.

Elastic term, Eq. (18), was added to account for the elastic strain effects that contribute to segregation:

$$\Delta H_{seg} = 0.71 \cdot \frac{1}{6} \cdot \left[ -\Delta H_{AinB}^{int} - \frac{c_0}{f} \gamma_B V_B^{\frac{2}{3}} + \frac{c_0}{f} \gamma_A V_A^{\frac{2}{3}} \right] - \Delta E_{st} \quad (22)$$

Equation (22) has no temperature and composition assumptions and contains readily available materials data.

Figure 12:
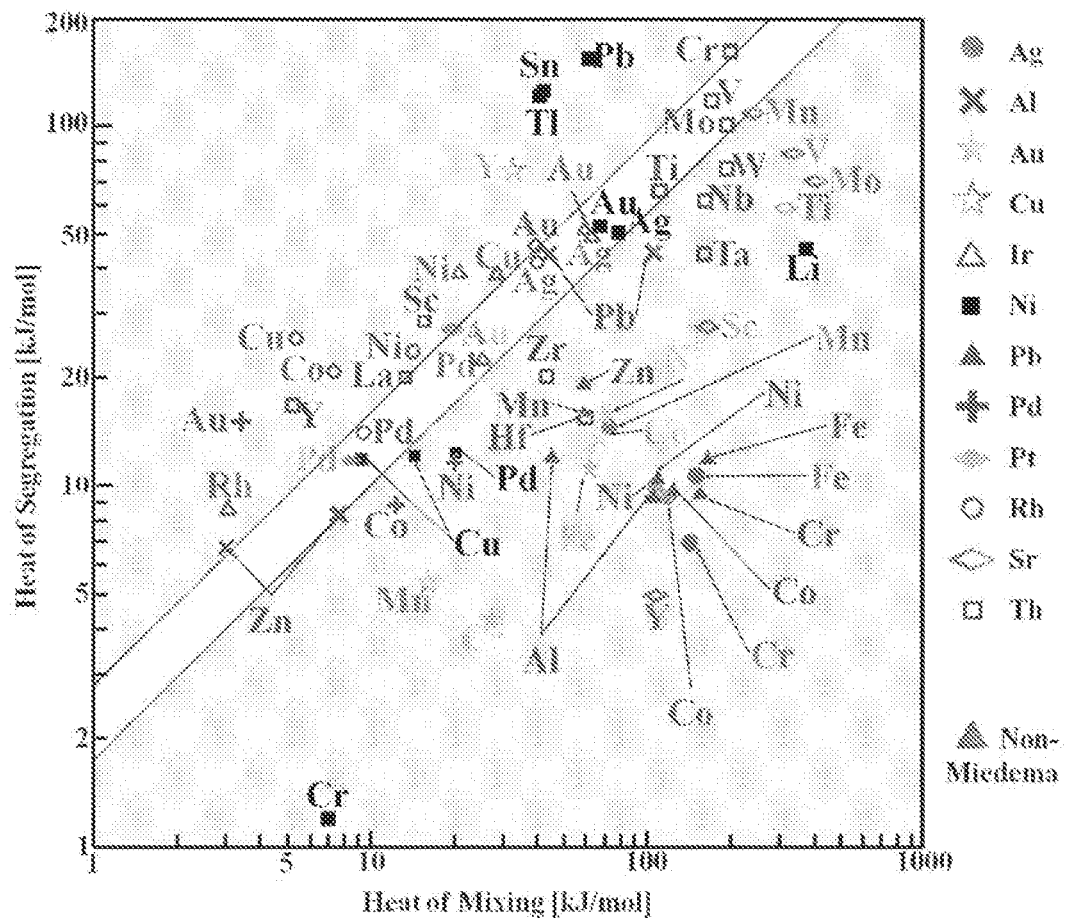
FIG. 12 shows a nanocrystalline stability map according to one embodiment for face-centered cubic (FCC) binary alloys at a temperature of 0.35 $T_{cr}$. Green region: stable NC microstructure; yellow region: metastable NC microstructure; red region: no stable NC microstructure.
Figure 13:
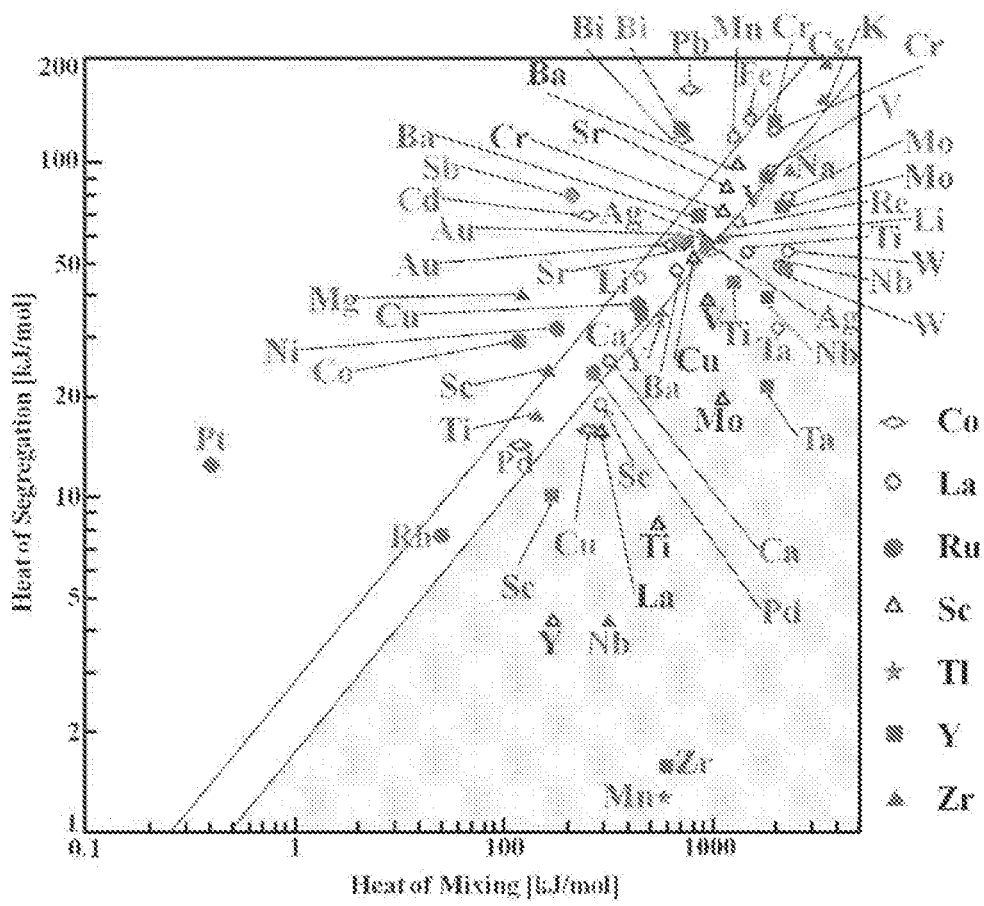
FIGS. 13(a)-13(b) show two exemplary nanocrystalline stability maps according to one embodiment for different hexagonal closed-pack (HCP) binary alloys at a temperature of 0.35 $T_{cr}$. Green region: stable NC microstructure; yellow region: metastable NC microstructure; red region: no stable NC microstructure.
Figure 13:
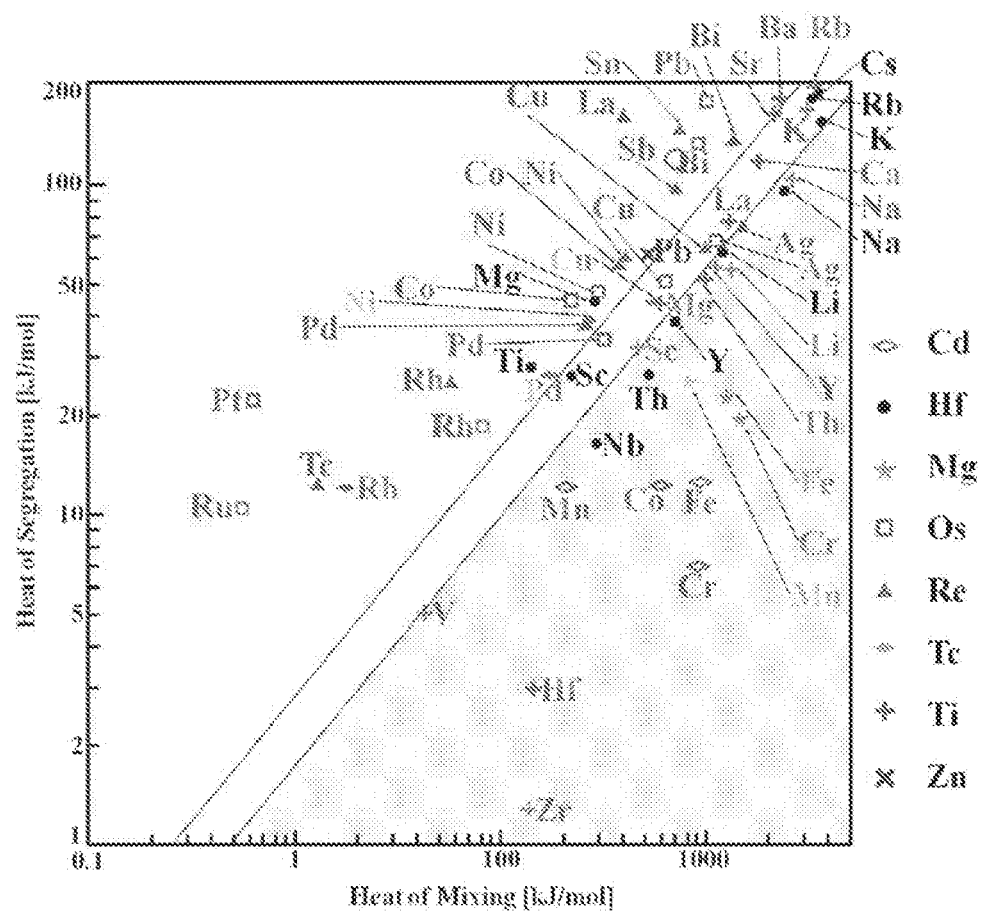
Figure 14:
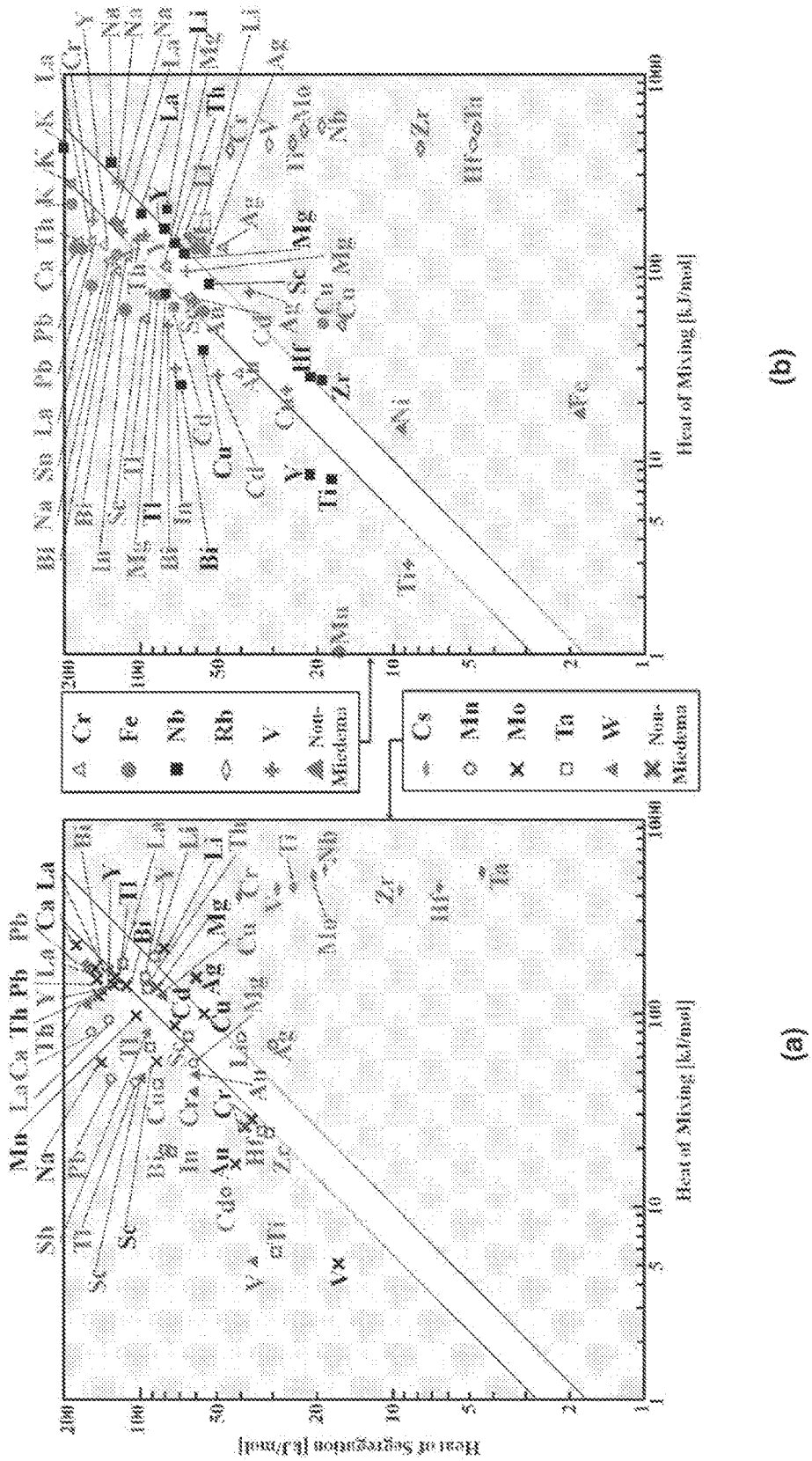
FIG. 14(a)-14(b) shows a nanocrystalline stability map according to one embodiment for body-centered cubic (BCC) binary alloys at a temperature of 0.35 $T_{cr}$. Green region: stable NC microstructure; yellow region: metastable NC microstructure; red region: no stable NC microstructure.

Resultant stability maps in some embodiments are provided in FIGS. 11-14. As further described below over 100 alloy compositions have been evaluated using the stability map provided herein. FIGS. 12-14 further separate the types of alloys shown on a stability man into FCC, HCP, and BCC, respectively; each of FIGS. 12-14 are constructed to illustrate stability behavior of binary alloys at a temperature of 0.35 Tcr. Green region: stable NC microstructure: yellow region: metastable NC microstructure; red region: no stable NC microstructure. Base alloy metal is described by the symbol and solute alloy is indicated by the accompanying matching color label. Alloys estimated with a model other than Miedema's are indicated with a red outline of the symbol.

Based on the calculations performed herein, including the results shown in FIGS. 12-14, it was determined that the following binary alloys may exist in a stable nanocrystalline phase against grain growth and phase separation: the alloys may be at least one of Al—Pb, Co—Bi, Co—Cd, Co—Pb, Cr—Au, Cr—Bi, Cr—La, Cr—Na, Cr—Pb, Cr—Sc, Cr—Sn, Cr—Th, Cr—Y, Cu—Y, Fe—Ba, Fe—Bi, Fe—Ca, Fe—Cd, Fe—In, Fe—La, Fe—Mg, Fe—Pb, Hf—Mg, Hf—Ti, Ir—Cu, Ir—Ni, Ir—Rh, La—Mn, Mn—Ba, Mn—Ca, Mn—Cd, Mn—La, Mn—Mg, Mn—Pb, Mn—Sr, Mn—Tl, Mo—Au, Mo—Cr, Mo—In, Mo—Na, Mo—Se, Mo—Th, Mo—V, Mo—Y, Nb—Bi, Nb—Cu, Nb—Ti, Nb—Tl, Nb—V, Ni—Pb, Ni—Sn, Ni—Tl Os—Bi, Os—Co, Os—Ni, Os—Pb, Os—Pt, Os—Rh, Os—Ru, Pb—Al, Pd—Au, Pt—Au, Re—Bi, Re—Co, Re—La, Re—Ni, Re—Pd, Re—Rh, Re—Sb, Re—Sn, Re—Tc, Rh—Au, Rh—Co, Rh—Cu, Rh—Ni, Ru—Bi, Ru—Co, Ru—Hg, Ru—Ni, Ru—Pt, Ru—Sb, Ta—Bi, Ta—Cu, Ta—Hf, Ta—In, Ta—Ti, Ta—Tl, Ta—Zr, Te—Ni, Te—Pd, Te—Rh, Th—La, Th—Sc, Th—Y, V—Bi, V—Cd, V—In, V—Ti, V—Tl, W—Au, W—Cr, W—In, W—Mn, W—Sb, W—Sc, W—Sn, W—Sr, W—Th, W—Ti, W—V, W—Y, W—Zn, Zn—Pb, Zr—Mg, Zr—Se; Cr—Cd, Fe—Au, Mo—Cd, Rh—Ag, V—Sc, Co—Au, La—Li, Ru—Au, Ru, Y—Sr; Mo—Ba, Mo—Pb, W—La, W—Pb, W—Sb, or combinations thereof. Other additional binary systems that have not been shown in the exemplary non-limiting maps provided herein may exist.

In one embodiment, based on the stability map, at a predetermined temperature of 1000 K, the following binary alloys may exist in a stable nanocrystalline phase against grown growth and phase separation: the alloys may be at least one of Co—Bi, Co—Cd, Co—Pb, Cr—Au, Cr—La, Cr—Na, Cr—Pb, Cr—Sc, Cr—Sn, Cr—Th, Cr—Y, Cu—Y, Fe—Ba, Fe—Bi, Fe—Ca, Fe—Cd, Fe—In, Fe—La, Fe—Mg, Fe—Pb, Hf—Mg, Ir—Cu, Ir—Ni, Mn—Ba, Mn—Ca, Mn—La, Mn—Mg, Mo—Pb, Mn—Sr, Mn—Tl, Mo—Ba, Mo—Cr, Mo—In, Mo—Na, Mo—Pb, Mo—Sc, Mo—Th, Nb—Bi, Nb—Cu, Nb—Tl, Ni—Pb, Ni—Sn, Ni—Tl, Os—Bi, Os—Co, Os—Ni, Os—Pb, Pt—Au, Re—Bi, Re—Co, Re—La, Re—Ni, Re—Pd, Re—Sb, Re—Sn, Rh—Au, Rh—Co, Rh—Cu, Rh—Ni, Ru—Bi, Ru—Co, Ru—Ni, Ru—Sb, Ta—Bi, Ta—Cu, Ta—Hf, Ta—In, Ta—Tl, Ta—Zr, Tc—Ni, Tc—Pd, V—Ba, V—Bi, V—Cd, V—Hg, V—In, V—Sr, V—Tl, W—Au, W—Cr, W—In, W—La, W—Mn, W—Pb, W—Sb, W—Sc, W—Sn, W—Sr, W—Th, W—Ti, W—Y, W—Zn, Zn—Pb, or combinations thereof. Other additional binary systems that have not been shown in the exemplary non-limiting maps provided herein may exist.

In one embodiment, based on the stability map, at a predetermined temperature of 0.35 $T_{cr}$, the following binary alloys may exist in a stable nanocrystalline phase against grown growth and phase separation: the alloys may be at least one of Al—Pb, Co—Bi, Co—Cd, Co—Pb, Cr—Au, Cr—Bi, Cr—La, Cr—Na, Cr—Pb, Cr—Sc, Cr—Sn, Cr—Th, Cr—Y, Cu—Y, Fe—Ba, Fe—Bi, Fe—Ca, Fe—Cd, Fe—In, Fe—La, Fe—Mg, Fe—Pb, Hf—Mg, Hf—Ti, Ir—Cu, Ir—Ni, Ir—Rh, La—Mn, Mn—Ba, Mn—Ca, Mn—Cd, Mn—La, Mn—Mg, Mn—Pb, Mn—Sr, Mn—Tl, Mo—Au, Mo—Cr, Mo—In, Mo—Na, Mo—Sc, Mo—Th, Mo—V, Mo—Y, Nb—Bi, Nb—Cu, Nb—Ti, Nb—Tl, Nb—V, Ni—Pb, Ni—Sn, Ni—Tl, Os—Bi, Os—Co, Os—Ni, Os—Pb, Os—Pt, Os—Rh, Os—Ru, Pb—Al, Pd—Au, Pt—Au, Re—Bi, Re—Co, Re—La, Re—Ni, Re—Pd, Re—Rh, Re—Sb, Re—Sn, Re—Te, Rh—Au, Rh—Co, Rh—Cu, Rh—Ni, Ru—Bi, Ru—Co, Ru—Hg, Ru—Ni, Ru—Pt, Ru—Sb, Ta—Bi, Ta—Cu, Ta—Hf, Ta—In, Ta—Ti, Ta—Tl, Ta—Zr, Tc—Ni, Tc—Pd, Tc—Rh, Th—La, Th—Sc, Th—Y, V—Bi, V—Cd, V—In, V—Ti, V—Tl, W—Au, W—Cr, W—In, W—Mn, W—Sb, W—Sc, W—Sn, W—Sr, W—Th, W—Ti, W—V, W—Y, W—Zn, Zn—Pb, Zr—Mg, Zr—Sc, or combination thereof. Other additional binary systems that have not been shown in the exemplary non-limiting maps provided herein may exist.

In one embodiment, based on the stability map, at a predetermined temperature of 0.5 $T_{cr}$, the following binary alloys may exist in a stable nanocrystalline phase against grown growth and phase separation: the alloys may be at least one of Al—Pb, Co—Bi, Co—Cd, Co—Pb, Cr—Au, Cr—Cd, Cr—Na, Cr—Sc, Cu—Y, Fe—Au, Fe—Ba, Fe—Cd, Fe—In, Fe—La, Fe—Mg, Hf—Mg, Hf—Ti, Ir—Cu, Ir—Ni, Ir—Rh, Mn—Ca, Mn—Cd, Mn—La, Mn—Mg, Mn—Pb, Mn—Tl, Mo—Au, Mo—Cd, Mo—Cr, Mo—In, Mo—Na, Mo—Sc, Mo—V, Nb—Bi, Nb—Cu, Nb—Ti, Nb—Tl, Nb—V, Ni—Pb, Ni—Sn, Ni—Tl, Os—Bi, Os—Co, Os—Ni, Os—Pb, Os—Pt, Os—Rh, Os—Ru, Pb—Al, Pd—Au, Pt—Au, Re—Co, Re—La, Re—Ni, Re—Pd, Re—Rh, Re—Sb, Re—Sn, Re—Tc, Rh—Ag, Rh—Au, Rh—Co, Rh—Cu, Rh—Ni, Ru—Bi, Ru—Co, Ru—Ni, Ru—Pt, Ru—Sb, Ta—Bi, Ta—Cu, Ta—Hf, Ta—In, Ta—Sc, Ta—Ti, Ta—Tl, Ta—Zr, Tc—Ni, Tc—Pd, Tc—Rh, Th—La, Th—Sc, Th—Y, V—Bi, V—Cd, Y—In, V—Sc, V—Ti, V—Tl, W—Au, W—Cr, W—Mn, W—Sb, W—Sc, W—Ti, W—V, W—Zn, Zn—Pb, Zr—Mg, or combinations thereof. Other additional binary systems that have not been shown in the exemplary non-limiting maps provided herein may exist.

In one embodiment, based on the stability map, at a predetermined temperature of 0.65 $T_{cr}$, the following binary alloys may exist in a stable nanocrystalline phase against grown growth and phase separation: the alloys may be at least one of Al—Pb, Co—Au, Co—Bi, Co—Cd, Cr—Au, Cr—Cd, Cr—Sc, Cu—Y, Fe—Au, Fe—Ba, Fe—Cd, Fe—In, Fe—Mg, Hf—Mg, Hf—Ti, Ir—Au, Ir—Cu, Ir—Ni, La—Li, Mn—Cd, Mn—Mg, Mn—Pb, Mn—Tl, Mo—Au, Mo—Cr, Mo—Na, Mo—Sc, Nb—Bi, Nb—Cu, Nb—Ti, Nb—Tl, Nb—V, Ni—Au, Ni—Pb, Ni—Sn, Ni—Tl, Os—Co, Os—Ni, Os—Pt, Os—Rh, Os—Ru, Pb—Al, Pd—Au, Re—Co, Re—La, Re—Ni, Re—Pd, Re—Rh, Re—Sb, Re—Sn, Re—Te, Rh—Ag, Rh—Au, Rh—Co, Rh—Cu, Rh—Ni, Ru—Au, Ru—Bi, Ru—Co, Ru—Ni, Ru—Pt, Ru—Sb, Ta—Bi, Ta—Hf, Ta—In, Ta—Sc, Ta—Ti, Ta—Tl, Ta—Zr, Tc—Ni, Tc—Pd, Tc—Rh, Th—Sc, Th—Y, V—Bi, V—Cd, V—In, V—Sc, V—Tl, W—Au, W—Cr, W—Mn, W—Sc, W—Ti, W—V, W—Zn, Y—Sr, Zn—Pb, Zr—Mg, or combinations thereof. Other additional binary systems that have not been shown in the exemplary non-limiting maps provided herein may exist.

In these embodiments, the range of compositions over which the desired nanocrystalline stable structure is obtained may be different. For example, it may occur at an alloy solute content of at least about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%. In some embodiments, the solute content may range from about 0.1% to about 48%—e.g., about 0.5% to about 45%, about 1% to about 40%, about 2% to about 38%, about 3% to about 36%, about 5% to about 34%, about 6% to about 32%, about 8% to about 30%, about 10% to about 28%, about 12% to about 26%, about 14% to about 24%, about 16% to about 22%, about 18% to about 20%. In some other embodiments, the solute content may range from about 0.5% to about 1% —e.g., about 2% to about 4%, about 4% to about 6%, about 6% to about 8%, about 8% to about 10%, about 12% to about 14%, about 14% to about 16% about 16% to about 18%, about 18% to about 20%, etc. Higher or lower percentages than those provided herein are also possible, depending on the materials. The percentage herein may refer to either volume percentage or mass percent, depending on the context.

The articles "a" and "an" are used herein to refer to one or to more than one (i.e., to at least one) of the grammatical object of the article. By way of example, "a polymer resin" means one polymer resin or more than one polymer resin. Any ranges cited herein are inclusive. The terms "substantially" and "about" used throughout this Specification are used to describe and account for small fluctuations. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

What is claimed:

1. A method of identifying and fabricating a stable phase of a binary alloy comprising a solute element and a solvent element, the method comprising:
   (A) determining at least a first thermodynamic parameter associated with grain growth of the binary alloy and a second thermodynamic parameter associated with phase separation of the binary alloy;
   (B) identifying the stable phase of the binary alloy based on the first thermodynamic parameter and the second thermodynamic parameter by comparing the first thermodynamic parameter and the second thermodynamic parameter with a predetermined set of respective thermodynamic parameters to identify the stable phase; and
   (C) subsequent to the identifying, fabricating the identified stable phase of the binary alloy;
   wherein the stable phase is one of a stable nanocrystalline phase, a metastable nanocrystalline phase, and a non-nanocrystalline phase.

2. The method of claim 1, wherein (A) comprises at least one of:
   calculating an enthalpy of mixing of the binary alloy as the second thermodynamic parameter,
   calculating an enthalpy of segregation of the binary alloy as the first thermodynamic parameter, and
   determining a third thermodynamic parameter that is a free energy of mixing as a function of at least one of (i)

concentration of grain boundary in the binary alloy, (ii) grain size of the binary alloy, (iii) concentration of the solute element in the binary alloy, and (iv) concentration of the solvent element in the binary alloy.

3. The method of claim 1, wherein the binary alloy has a positive enthalpy of mixing, and at least one of the at least two thermodynamic parameters is determined with an assumption that the binary alloy is a non-dilute binary alloy.

4. The method of claim 1, wherein the binary alloy has a lattice arrangement that is face-centered cubic, body-centered cubic, or hexagonal closed-packed.

5. The method of claim 1, wherein in (A) the first thermodynamic parameter and the second thermodynamic parameter are determined at a predetermined temperature selected from 1000 K, 0.35 $T_{cr}$ of the binary alloy, 0.5 $T_{cr}$ of the binary alloy, and 0.65 $T_{cr}$ of the binary alloy.

6. The method of claim 1, wherein in the case where the stable phase is the stable nanocrystalline phase, the method further comprises identifying the stable phase of the binary alloy as one of dual-phase nanocrystalline, dual-phase nanocrystalline and amorphous phase; amorphous phase; and a classical segregation-stabilized nanocrystalline phase.

7. A system comprising (i) at least one memory storing processor-executable instructions and (ii) at least one information processor coupled to the at least one memory, wherein upon execution of the processor-executable instructions the processor implements the method recited in claim 1.

* * * * *

UNITED STATES PATENT AND TRADEMARK OFFICE
CERTIFICATE OF CORRECTION

PATENT NO. : 10,234,410 B2
APPLICATION NO. : 14/384518
DATED : March 19, 2019
INVENTOR(S) : Heather A. Murdoch et al.

Page 1 of 1

It is certified that error appears in the above-identified patent and that said Letters Patent is hereby corrected as shown below:

In the Specification

At Column 1, Lines 8-11, in the paragraph under the heading "STATEMENT REGARDING FEDERALLY SPONSORED RESEARCH":
"This invention was made with Government support under Grant Nos. W911NF-07-D-0004, W911QX-09-P-0009 and W911NF-09-1-0422 awarded by the United States Army. The Government has certain rights in the invention."

Should read:
--This invention was made with government support under W911QX-09-P-0009, W911NF-09-1-0422, and W911NF-07-D-0004 awarded by the U.S. Army Research Office. The government has certain rights in the invention.--

Signed and Sealed this
First Day of August, 2023

Katherine Kelly Vidal
*Director of the United States Patent and Trademark Office*